(12) United States Patent
Maris

(10) Patent No.: US 7,782,471 B2
(45) Date of Patent: *Aug. 24, 2010

(54) OPTICAL METHOD FOR THE CHARACTERIZATION OF LATERALLY-PATTERNED SAMPLES IN INTEGRATED CIRCUITS

(75) Inventor: Humphrey J. Maris, Barrington, RI (US)

(73) Assignee: Brown University, Providence, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 12/381,640

(22) Filed: Mar. 13, 2009

(65) Prior Publication Data

US 2009/0213375 A1    Aug. 27, 2009

Related U.S. Application Data

(60) Continuation of application No. 12/072,841, filed on Feb. 28, 2008, now Pat. No. 7,505,154, which is a division of application No. 09/969,336, filed on Oct. 1, 2001, now Pat. No. 7,339,676, which is a division of application No. 09/404,939, filed on Sep. 23, 1999, now Pat. No. 6,321,601, which is a continuation-in-part of application No. 08/954,347, filed on Oct. 17, 1997, now Pat. No. 5,959,735, which is a division of application No. 08/689,287, filed on Aug. 6, 1996, now Pat. No. 5,748,318.

(51) Int. Cl.
*G01B 11/28* (2006.01)

(52) U.S. Cl. ..................... 356/630; 356/369

(58) Field of Classification Search ......... 356/432–440, 356/445, 319, 625–632, 502, 503, 496, 364–369
See application file for complete search history.

(56) References Cited

U.S. PATENT DOCUMENTS

| 3,950,987 | A | 4/1976 | Slezinger et al. ......... 73/141 A |
| 4,484,820 | A | 11/1984 | Rosencwaig .................... 374/6 |
| 4,522,510 | A | 6/1985 | Rosencwaig et al. .......... 374/7 |
| 4,579,463 | A | 4/1986 | Rosencwaig et al. ......... 374/57 |

(Continued)

FOREIGN PATENT DOCUMENTS

WO    WO 98 22801 A1    5/1998

(Continued)

OTHER PUBLICATIONS

D.A. Young et al., "Heat Flow in Glasses on a Picosecond Timescale", Dept. of Engineering, Brown University, Providence, RI 1986, p. 49-51.

(Continued)

*Primary Examiner*—Hoa Q Pham
(74) *Attorney, Agent, or Firm*—Harrington & Smith

(57) ABSTRACT

Disclosed is a method for characterizing a sample having a structure disposed on or within the sample, comprising the steps of applying a first pulse of light to a surface of the sample for creating a propagating strain pulse in the sample, applying a second pulse of light to the surface so that the second pulse of light interacts with the propagating strain pulse in the sample, sensing from a reflection of the second pulse a change in optical response of the sample, and relating a time of occurrence of the change in optical response to at least one dimension of the structure.

23 Claims, 17 Drawing Sheets

U.S. PATENT DOCUMENTS

| | | | |
|---|---|---|---|
| 4,632,561 A | 12/1986 | Rosencwaig et al. | 356/432 |
| 4,636,088 A | 1/1987 | Rosencwaig et al. | 374/5 |
| 4,679,946 A | 7/1987 | Rosencwaig et al. | 374/5 |
| 4,710,030 A | 12/1987 | Tauc et al. | 356/32 |
| 4,750,822 A | 6/1988 | Rosencwaig et al. | 356/445 |
| 4,795,250 A | 1/1989 | Schuur et al. | 356/400 |
| 4,844,617 A | 7/1989 | Kelderman | 356/372 |
| 4,854,710 A | 8/1989 | Opsal et al. | 356/432 |
| 4,952,063 A | 8/1990 | Opsal et al. | 356/432 |
| 4,999,014 A | 3/1991 | Gold et al. | 356/382 |
| 5,042,951 A | 8/1991 | Gold et al. | 356/369 |
| 5,042,952 A | 8/1991 | Opsal et al. | 356/432 |
| 5,074,669 A | 12/1991 | Opsal | 356/445 |
| 5,083,869 A | 1/1992 | Nakata et al. | 356/432 |
| 5,227,912 A | 7/1993 | Ho et al. | 359/578 |
| 5,379,109 A | 1/1995 | Gaskill et al. | 356/445 |
| 5,481,475 A | 1/1996 | Young | 364/578 |
| 5,523,840 A | 6/1996 | Nishizawa et al. | 356/355 |
| 5,546,811 A | 8/1996 | Rogers et al. | 73/800 |
| 5,574,562 A | 11/1996 | Fishman et al. | 356/432 |
| 5,585,921 A | 12/1996 | Pepper et al. | 356/357 |
| 5,633,711 A | 5/1997 | Nelson et al. | 356/318 |
| 5,706,094 A | 1/1998 | Maris | 356/432 |
| 5,748,317 A | 5/1998 | Maris et al. | 356/357 |
| 5,748,318 A | 5/1998 | Maris et al. | 356/381 |
| 5,864,393 A | 1/1999 | Maris | 356/28 |
| 5,959,735 A | 9/1999 | Maris et al. | 356/632 |
| 6,008,906 A | 12/1999 | Maris | 356/432 |
| 6,025,918 A * | 2/2000 | Maris | 356/388 |
| 6,038,026 A | 3/2000 | Maris | 356/514 |
| 6,057,927 A | 5/2000 | Levesque et al. | 356/432 T |
| 6,081,330 A | 6/2000 | Nelson et al. | 356/318 |
| 6,191,855 B1 | 2/2001 | Maris | 356/244 |
| 6,208,418 B1 | 3/2001 | Maris | 356/388 |
| 6,211,961 B1 | 4/2001 | Maris | 356/432 |
| 6,317,216 B1 | 11/2001 | Maris | 356/496 |
| 6,321,601 B1 | 11/2001 | Maris | 73/657 |
| 6,563,591 B2 | 5/2003 | Maris | 356/496 |
| 7,339,676 B2 * | 3/2008 | Maris | 356/432 |
| 7,505,154 B2 * | 3/2009 | Maris | 356/630 |

FOREIGN PATENT DOCUMENTS

| | | |
|---|---|---|
| WO | WO 98 22815 | 5/1998 |

OTHER PUBLICATIONS

D.H. Auston et al., "Picosecond Ellipsometry of Transient Electron-Hole Plasmas in Germanium", Physical Review Letters, vol. 32, No. 20 May 20, 1974, p. 1120-1123.

R.J. Stoner et al., "Kapitza Conductance and Heat Flow Between Solids at Temperatures from 50 to 300K", Physical Review 8, vol. 48, No. 22, Dec. 1, 1993, p. 16 373-16387.

R.J. Stoner et al., "Measurements of Kapitza Conductance Between Diamond and Several Metals", Physical Review Letters vol. 68, No. 10, Mar. 9, 1992, p. 1563-1566.

S. Sumie et al., "A New Method of Photothermal Displacement Measurement by Laser Interferometric Probe", Jpn. J. Appl.. Phys. vol. 31, Pt. 1 No. 11, 1992, p. 3575-3583.

S. Sumie et al. J. Appl. Phys. 76(10), Nov. 15, 1994, p. 5681-5689.

F.E. Doany et al., "Carrier Lifetime Versus Ion-Implementation Dose in Silicon on Sapphire", Appl. Phys. Lett. 50(8), Feb. 23, 1987, p. 460-462.

Search Report for Application No. PCT/US00/23059, Dated Aug. 23, 2000.

W. Lee Smith et al., "Ion Implant Monitoring with Thermal Wave Technology", Appl. Phys. Lett., vol. 47 No. 6, Sep. 15, 1985, p. 584-586.

J. Opsal et al. "Thermal and Plasma Wave Dept Profiling in Silicon" Appl. Physl. Lett. vol. 47, No. 5, Sep. 1, 1985, p. 498-500.

A.Rosencwaig et al. "Thin-Film Thickness Measurements with Thermal Waves", Appl. Phys. Lett., vol. 43 No. 2, Jul. 15, 1983, p. 166-168.

A. Rosencwaig et al. "Detection of Thermal Waves Through Optical Reflectance", Appl. Phys. Lett., vol. 46, No. 11, Jun. 1, 1985, p. 1013-1015.

A. Elci et al. "Physics of Ultrafast Phenomena in Solid State Plasmas", Solid-State Electronics, vol. 21, 1978, p. 151-158.

D.H. Auston et al., "Picosecond Spectroscopy of Semiconductors", Solid State Electronics, vol. 21, 1978; p. 147-150.

* cited by examiner

US 7,782,471 B2

OPTICAL METHOD FOR THE CHARACTERIZATION OF LATERALLY-PATTERNED SAMPLES IN INTEGRATED CIRCUITS

CROSS-REFERENCE TO A RELATED APPLICATION

This patent application is a continuing application of U.S. application Ser. No. 12/072,841, filed Feb. 28, 2008 now U.S. Pat. No. 7,505,154, which is a divisional application of U.S. application Ser. No. 09/969,336, filed Oct. 1, 2001, which issued as U.S. Pat. No. 7,339,676, which is a division of U.S. application Ser. No. 09/404,939, filed Sep. 23, 1999, which issued as U.S. Pat. No. 6,321,601, which is a continuation-in-part of application Ser. No. 08/954,347, filed Oct. 17, 1997, which issued as U.S. Pat. No. 5,959,735, which is a division of application Ser. No. 08/689,287, filed Aug. 6, 1996, which issued as U.S. Pat. No. 5,748,318. The disclosure of each application is incorporated by reference in its entirety insofar as it does not conflict with the teachings of the present invention.

This invention was made with government support under grant number DEFG02-ER45267 awarded by the Department of Energy. The government has certain rights in the invention.

FIELD OF THE INVENTION

This invention relates generally to optical metrology methods and apparatus and, more particularly, to optical techniques that use picosecond scale light pulses for characterizing samples.

BACKGROUND-OF-THE INVENTION

Currently, in the semiconductor industry there is a great interest in the characterization of thin films and small structures. Integrated circuits are made up of a large number of patterned thin films deposited onto a semiconductor substrate, such as silicon. The thin films include metals to make connections between the transistors making up the chip, and insulating films to provide insulation between the metal layers (see: S. A. Campbell, The Science and Engineering of Microelectronic Fabrication, Oxford University Press, (1996)). The metal films (interconnects) are typically arranged as a series of patterned layers. At the present time there may be 4 or 5 layers of interconnects. It is likely that as more complex integrated circuits are developed, requiring a greater number of interconnections, the number of layers will increase. Metals of current interest include, for example, aluminum, copper, titanium and silicides. Insulating films include, for example, oxide glasses of various compositions and polymers. The films may be patterned so as to form wires running across the surface of the sample. For convenience, each such wire shall be referred to as a structure. These wires may be embedded into a film of another material or may be deposited on top of another film. For some samples of interest, all of the wires have the same nominal dimensions, run in the same direction across the surface of the sample, and are equally spaced. If the wires run in the direction parallel to the z-axis, for example, the geometry of the sample is entirely specified when the cross-section in the x-y plane is determined (see FIG. 1). For this reason such samples are referred to as two-dimensional patterned structures. Another type of sample of interest might include a two-dimensional array of identical rectangular parallelepipeds disposed on a surface (see. FIG. 2). The geometry of such a sample cannot be completely specified by determining the geometry in a single x-y plane. For this reason, a sample of this type is referred to as a three-dimensional patterned sample. Other samples might still be periodic, but with a more complicated pattern. For example, the sample could be made up of a sequence ABABAB, of wires with two different dimensions, such that wire A has width $a_A$ and height $b_A$, and wire B has width $a_B$ and height $b_B$. Alternately, the sample could include a sequence of wires, all of which have the same geometry, but the spacing between the wires could alternate between the values $c_1$ and $c_2$.

In the production of integrated circuits it is essential that all aspects of the fabrication process be controlled as closely as possible. It is important to measure the geometry of the sample, i.e., the thickness of thin films, the lateral dimensions of wire structures such as the dimensions a, and b in FIG. 1, the spacing c between structures, etc. It is also important to be able to measure mechanical and electrical properties of the structure, such as the adhesion between a wire and the film it is in contact with.

There are a number of techniques currently available for the determination of the geometry of such samples. These include:

(1) Scanning Electron Microscopy. In this technique an electron beam is focused onto a small spot on the sample, and electrons that are scattered from the sample surface are detected. The electron beam is scanned across the surface of the sample, and an image of the sample surface is obtained. For a two-dimensionally patterned sample this technique can determine the dimensions a and c as shown in FIG. 1. For a three-dimensionally patterned sample the dimensions $a_1$, $a_2$, $c_1$, and $c_2$ of FIG. 2 can be determined. This method cannot be used to determine the dimension b of FIG. 1. In addition, the method is time consuming since the sample must be placed into the high vacuum chamber of the electron microscope. In addition, to measure dimensions with scanning electron microscopy it is necessary to perform a careful calibration of the instrument.

(2) Scanning Electron Microscopy with Sectioning. In this technique, material is removed from the sample to expose a section of the sample lying in the xy-plane. Scanning electron microscopy is then used to view this section of the sample. This method is thus able to measure the dimension b shown in FIGS. 1 and 2. This method has the following disadvantages: i) A considerable amount of time is required to prepare the sample. ii) The sample has to be destroyed in order to make the measurement. iii) The method is time-consuming since the sample has to be transferred into the high-vacuum chamber of the electron microscope in order for the measurement to be made.

(3) Atomic Force Microscopy. In this technique an atomic force microscope is used instead of an electron microscope to view the surface of the sample. The top surface of the sample can be viewed directly, as in (1) above, and measurements can also be made after sectioning the sample as in method (2). This method has the disadvantage that a considerable amount of time is involved for the measurements to be made. In addition, if the sample is sectioned, it is destroyed.

OBJECTS OF THE INVENTION

It is a first object of this invention to provide a method for the rapid determination of the dimensions of samples composed of one or more structures, or a periodic array of structures, deposited directly onto a substrate, or onto a film deposited on a substrate, or embedded within a film or within the substrate.

It is a second object of this invention to provide a method that does not require the destruction of such samples.

It is a further object of this invention to determine mechanical and electrical properties of such samples.

SUMMARY OF THE INVENTION

In accordance with a first method of the present invention, a method is provided for characterizing a sample having a structure that is disposed on or within the sample. The method comprises the steps of applying a first pulse of light to a surface of the sample for creating a propagating strain pulse in the sample, applying a second pulse of light to the surface so that the second pulse of light interacts with the propagating strain pulse in the sample, sensing from a reflection of the second pulse a change in optical response of the sample, and relating a time of occurrence of the change in optical response to a dimension of the structure.

In accordance with a second method of the present invention, a method is provided for characterizing a sample having a structure that is disposed on or within the sample. The method comprises the steps of applying a first pulse of light to a surface of the sample to excite the structure into a normal mode of vibration, applying a second pulse of light to the surface, sensing from a reflection of the second pulse a change in optical response of the sample, relating the change in optical response to an oscillatory component of the vibration; and relating the oscillatory component to a spatial or electrical characteristic of the structure.

In accordance with a first embodiment of the present invention, a non-destructive system is provided for characterizing a sample having a structure that is disposed on or within the sample. The system comprises an optical beam generator for applying a first pulse of light to a surface of the sample for creating a propagating strain pulse in the sample, an optical beam generator for applying a second pulse of light to the surface so that the second pulse of light interacts with the propagating strain pulse in the sample, a sensor for sensing from a reflection of the second pulse a change in optical response of the sample, and a processor for relating a time of occurrence of the change in optical response to a dimension of the structure.

In accordance with a second embodiment of the present invention, a non-destructive system is provided for characterizing a sample having a structure that is disposed on or within the sample. The system comprises an optical beam generator for applying a first pulse of light to a surface of the sample to excite the structure into a normal mode of vibration, an optical beam generator for applying a second pulse of light to the surface, a sensor for sensing from a reflection of the second pulse a change in optical response of the sample, a processor for relating the change in optical response to an oscillatory component of the vibration, and a processor for relating the oscillatory component to a spatial or electrical characteristic of the structure.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 1:
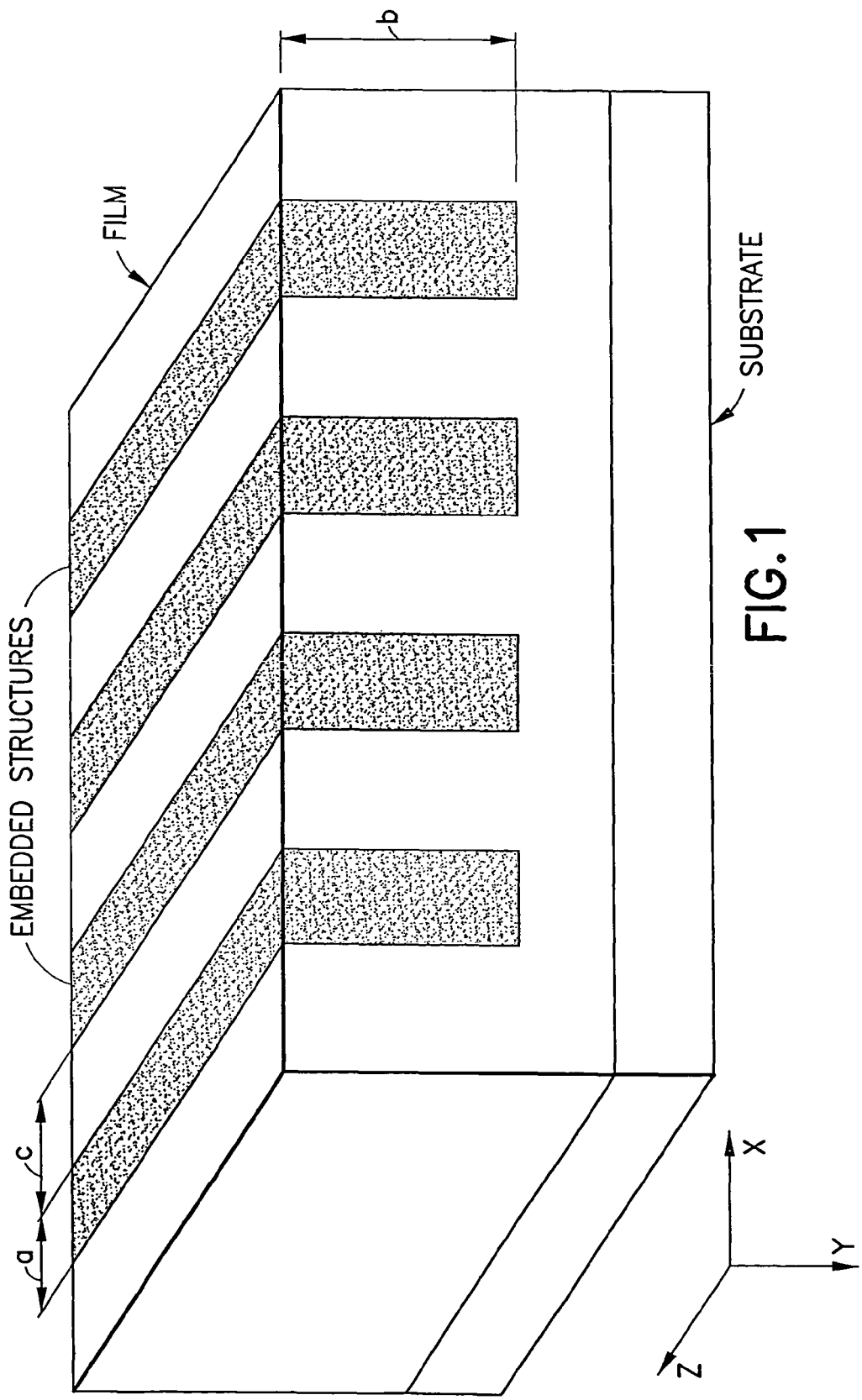
FIG. 1 is an illustration of a two-dimensional patterned structure.
Figure 2:
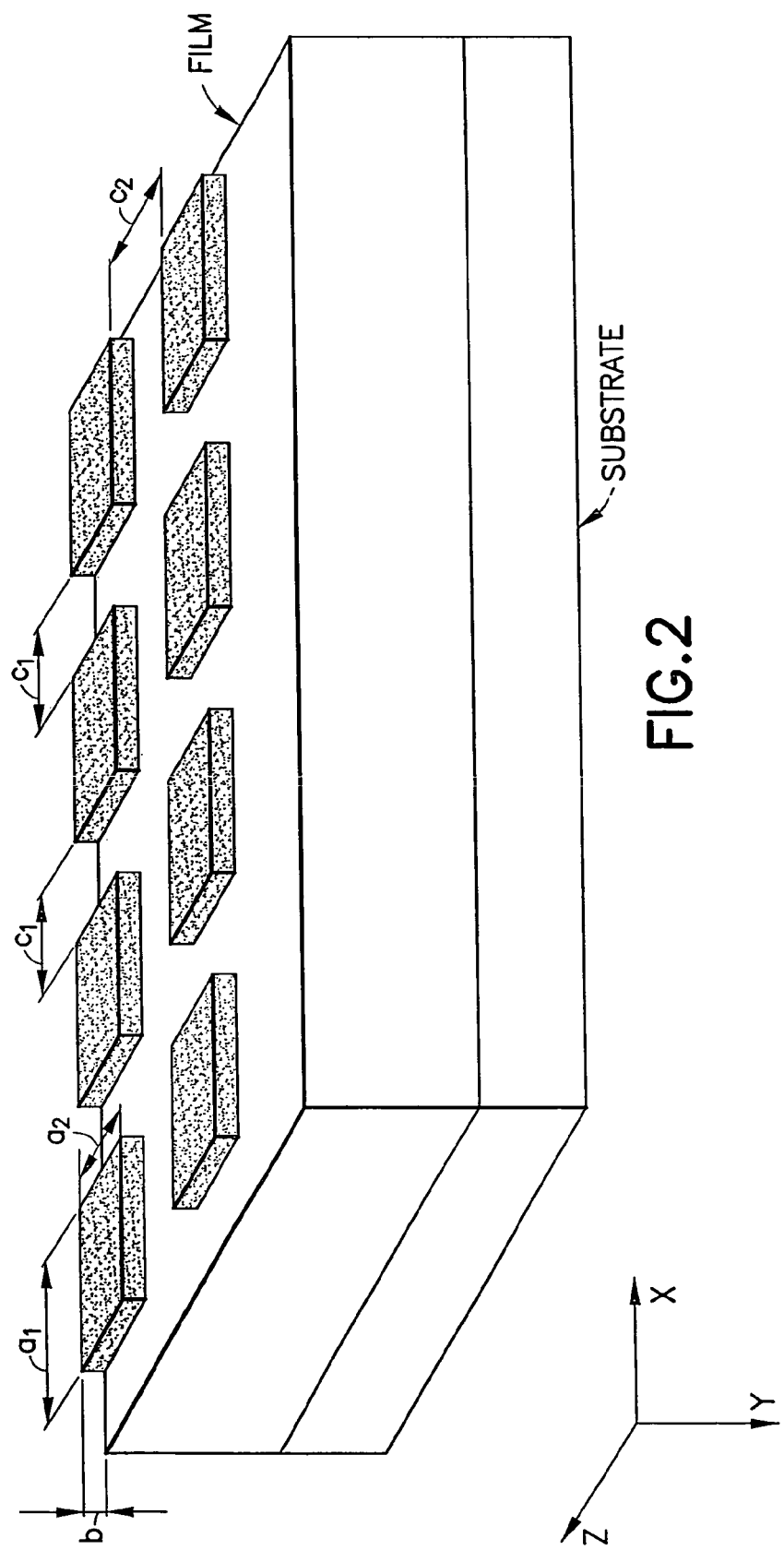
FIG. 2 is an illustration of a three-dimensional patterned sample, and more specifically, a two-dimensional array of elements disposed on a surface.

The teaching of this invention is practiced with an optical generator and a detector of a stress wave within a sample. The sample is comprised of a substrate having a structure, or an array of similar, but not necessarily identical, structures deposited on it. These structures may be located directly on top of the substrate, or may be embedded in the substrate, or may be deposited on top of one of a film, or films, deposited on the substrate, or may be embedded in one of these films. The structures may be composed of a single material, such as copper or aluminum or silicon, or may be composed of more than one material. The structures may be in the form of wires running in a particular direction across the sample; this type of sample is referred to as a two-dimensionally patterned sample (2D), or as a sample composed of wire structures. An example of this type of sample is shown in FIG. 1. Note that although the length of the wires is finite, this length is assumed to be much larger than the spacing between the wires, or the height of the wires (dimension b). The sample may also include an array of elements forming a grid pattern on the surface of the substrate or film. This is referred to as a three-dimensionally patterned sample (3D) or as a sample composed of dot structures. Again, this pattern is repeated over an area with dimensions large compared to the dimensions of each individual structure. The lateral dimensions of each structure, e.g., the width for a wire structure, could range from 30 Å to 10 microns, and the height of the structure, e.g., the dimension b shown in FIG. 1 or 2 could range from 30 Å to 10 microns.

Reference may also be made to commonly assigned application Ser. No. 09/111,456, filed on Jul. 7, 1997, which issued as U.S. Pat. No. 6,025,918. The disclosure of which is incorporated by reference in its entirety insofar as it does not conflict with the teachings of the present invention.

In this system, a non-destructive first light pulse is directed onto the sample. This first light pulse, referred to hereafter as a pump beam, is absorbed in a thin layer on the surface of the sample. According to the angle at which the pump beam is incident onto the surface of the sample, the material making up the structures, the films and the substrate, the light may be mostly absorbed in the top of each structure, the sides of the structure, one of the films, or in the substrate itself. When the pump beam is absorbed, the temperature of the surface layer is increased, and the layer tries to expand. This launches a strain pulse that propagates through the sample. The direction in which the strain pulse propagates is determined by the orientation of the surface from which the pulse originates. For example, if the structures have vertical side walls and light is absorbed in a thin layer adjacent to these walls, a strain pulse is generated that propagates in the direction parallel to the surface of the substrate. On the other hand if each structure has a flat top and light is absorbed in the region near to this surface, the strain pulse propagates in the direction normal to the plane of the substrate. In many types of sample, strain pulses with appreciable amplitude are generated in a number of different regions of the sample, and propagate in different directions.

The strain pulses propagate through the structures, the film, or films, and in the substrate. When a strain pulse reaches an interface between dissimilar materials, a fraction of the pulse is reflected and a fraction is transmitted. There is thus a time-dependent strain within the sample. This strain results in a change in the optical constants, real and imaginary parts of the dielectric constant, of the sample material, as a consequence of a piezo-optic effect. In addition, there is a change in geometry of the sample. For example, the width of the wire structures in a 2D sample, i.e., dimension a of FIG. 1, is affected by the strain and varies with time. The change in the optical constants and the change in the geometry results in a change $\Delta R(t)$ in the optical reflectivity R of the sample. The time t here indicates the time that has elapsed since the application of the pump pulse.

The fact that there is a change in geometry of the structure as a result of the propagation of the strain pulses affects the choice of wavelengths for the probe beam. For example, it is known, see U. Gerhardt, Physical Review, 172, p. 651-664, 1968, that for copper the change in the optical constants in the wavelength range 7000-8000 Å when a strain is applied is very small. Thus for a planar copper film, it is hard to make measurements using a probe beam with a wavelength in this range. However, for a laterally-patterned sample, it has been demonstrated that with a probe beam in this wavelength range there can be a large change $\Delta R(t)$ in the optical reflectivity. It is believed that this large change comes about because the strain pulses propagating in the sample result in a time-dependent change in the size of the structures, and hence also in the spacing between them.

This change $\Delta R(t)$ is measured by means of a second light pulse directed at the sample. This second light pulse, referred to hereafter as a probe beam, is time-delayed relative to the pump beam. Properties of the sample are determined by analysis of the transient optical response, e.g., changes in the reflected probe beam intensity.

Figure 3:
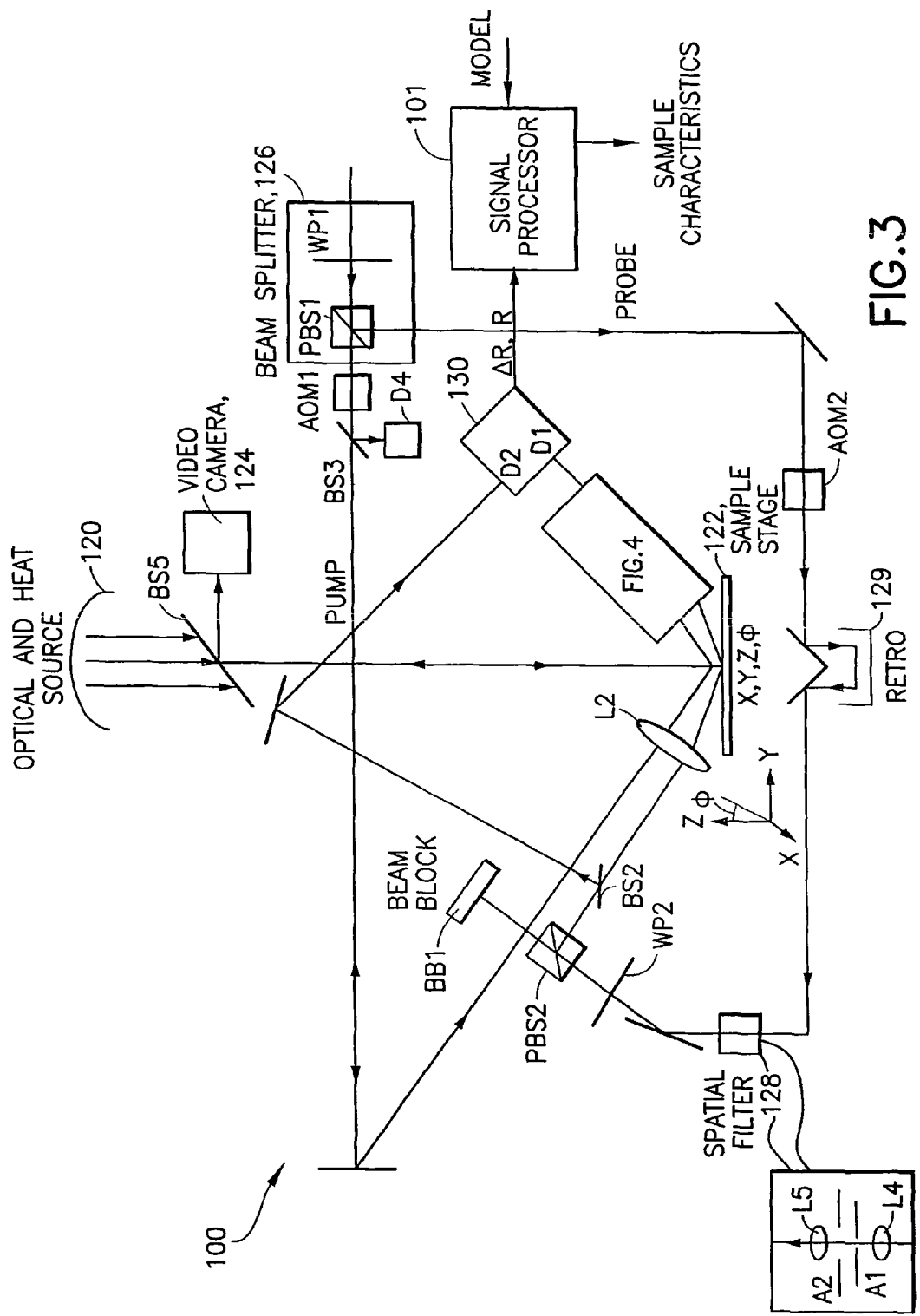
FIG. 3 is a block diagram of one embodiment of an ultra-fast optical system that is suitable for use in practicing this invention, specifically, a parallel, oblique beam embodiment.
Figure 4:
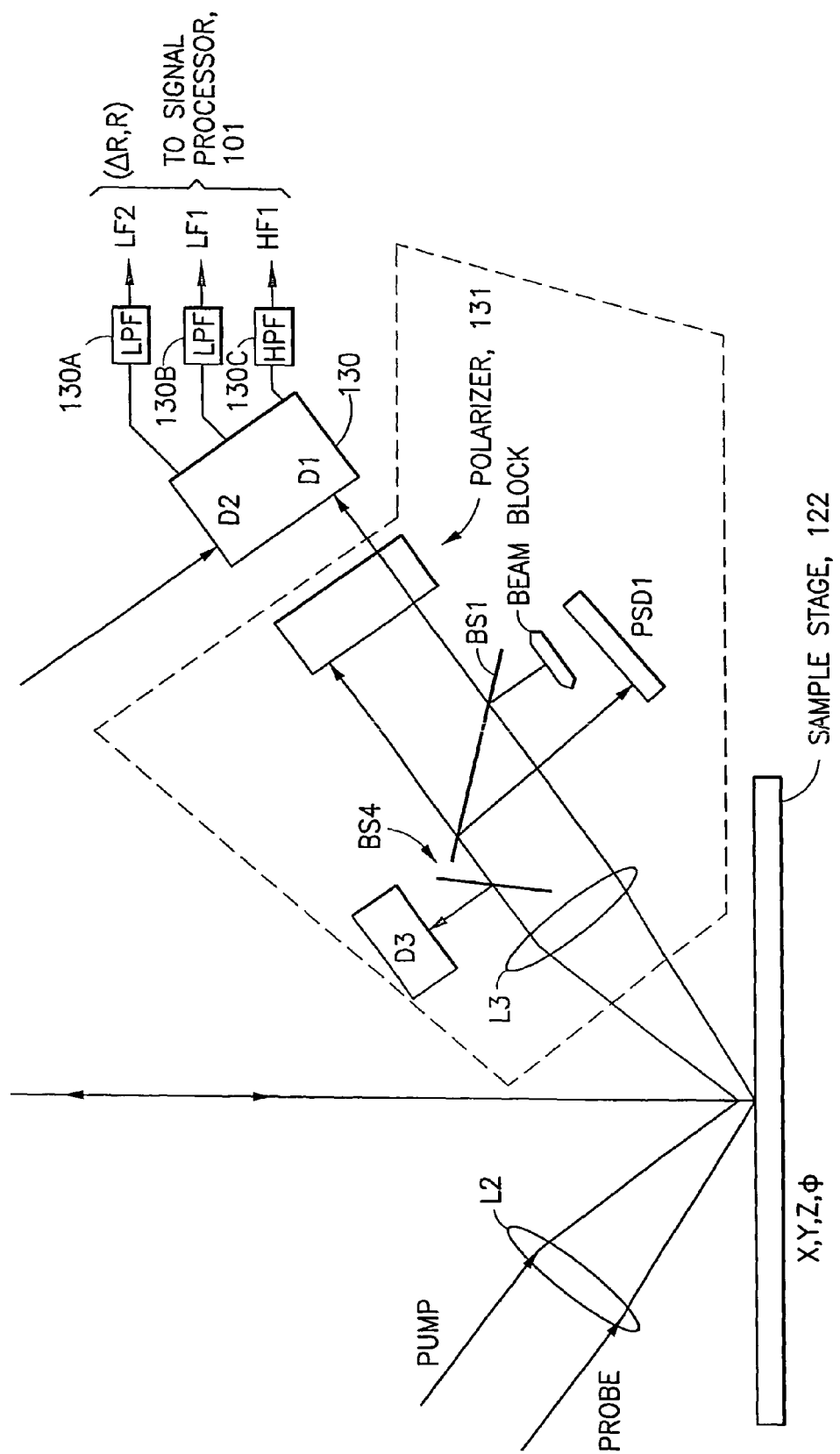
FIG. 4 illustrates a portion of FIG. 3 in greater detail.

Reference is now made to FIG. 3 and FIG. 4 for illustrating a first embodiment of an apparatus 100 suitable for practicing this invention. This embodiment is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in a sample stage 122. One advantage of the optical heater is that it makes possible rapid sequential measurements at different temperatures, or at one stabilized temperature.

The video camera 124 provides a displayed image for an operator, and facilitates the set-up of the measurement system. Appropriate pattern recognition software can also be used for this purpose, thereby minimizing or eliminating operator involvement. BS5 is a broad band beam splitter that directs video and a small amount of laser light to the video camera 124. The camera 124 and processor 101 can be used to automatically position the pump and probe beams on a measurement site.

The sample stage 122 is preferably a multiple-degree of freedom stage that is adjustable in height (global z-axis), position (global x and y-axes), and optionally tilt (φ), and allows motor controlled positioning of a portion of the sample relative to the pump and probe beams. The global z-axis is used to translate the sample vertically into the focus region of the pump and probe, the global x and y-axes translate the sample parallel to the focal plane, and the tilt axes adjust the orientation of the stage 122 to establish a desired angle of incidence for the probe beam. This is achieved via a first position sensitive detector PSD1 and a signal processor 101, as shown in FIG. 3 and described below.

In an alternative embodiment, the optical head may be moved relative to a stationary, tiltable stage 122' (not shown). This is particularly important for scanning large objects, such as 300 mm diameter wafers. In this embodiment the pump beam, probe beam, and video signal can be delivered to or from a translatable head via optical fibers or fiber bundles.

A pump-probe beam splitter 126 splits an incident laser beam pulse, preferably of picosecond or shorter duration, into pump and probe beams, and includes a rotatable half-wave plate (WP1) that rotates the polarization of the unsplit beam. WP1 is used in combination with a polarizing beam splitter PBS1 to effect a continuously variable split between pump and probe power. This split may be controlled by the computer by means of a motor to achieve an optimal signal to noise ratio for a particular sample. The appropriate split depends on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of modulator AOM1. The use of AOM2 is optional in the system illustrated in FIG. 3. Optionally, the AOMs may be synchronized to a common clock source, and may further be synchronized to the pulse repetition rate (PRR) of the laser that generates the pump and probe beams. Optionally an electro-optic modulator can be used in place of acousto-optic modulators AOM1 or AOM2.

A spatial filter 128 is used to preserve at its output a substantially invariant probe beam profile, diameter, and propagation direction for an input probe beam which may vary due to the action of the mechanical delay line shown as a retroreflector 129. The spatial filter 128 includes a pair of apertures A1 and A2, and a pair of lenses L4 and L5. An alternative embodiment of the spatial filter incorporates an optical fiber, as described above. If the profile of the probe beam coming from the mechanical delay line does not vary appreciably as the retroreflector 129 is moved, the spatial filter 128 can be omitted.

WP2 is a second adjustable halfwave plate which functions in a similar manner with PBS2 to the WP1/PBS1 combination of the beam splitter 126. A part of the probe beam passing through beam splitter PBS2 impinges on a beam block BB1. Beam splitter BS2 is used to direct a small fraction of the probe beam onto reference detector D2. The output of D2 is amplified and sent through a low pass filter 130A to give an electrical signal LF2, which is proportional to the average intensity of the incident probe beam.

The probe beam after passing through BS2 is focused onto the sample by lens L2. As shown in FIG. 4, after reflection from the sample the beam is collimated and after passing polarizer 131 is incident on photodetector D1. From the output of D1 two electrical signals are derived. The first signal LF1 is obtained by passing the amplified output of D1 through a low pass filter 130B to give an electrical signal proportional to the average intensity of the incident probe beam. The second signal HF1 is obtained by passing the amplified output of D1 through a high pass filter 130C that passes the frequency of modulation used for AOM1.

The low frequency signals LF1 and LF2 can be used to determine the reflectivity of the sample, after allowance is made for fixed losses in both optical paths. The signal LF2 and the average (dc) output of detector D4 give a measure of the intensity of the pump and probe beams. These signals are fed to a computer, for example, the signal processor 101, which in turn controls motorized waveplates WP1 and WP2. The computer is programmed to adjust these waveplates so as to give the desired total optical power and pump/probe ratio for a sample exhibiting a particular reflectivity.

The linear polarizer 131 is employed to block scattered pump light polarization, and to pass the probe beam. The beam splitter BS1 is used to direct a small part of the pump beam, and optionally a small part of the probe beam, onto first Position Sensitive Detector (PSD1) that is used for autofocusing, in conjunction with the processor 101 and movements of the sample stage 122. The PSD1 is employed in combination with the processor 101 and the computer-controlled stage 122 (tilt and z-axis) to automatically focus the pump and probe beams onto the sample to achieve a desired focusing condition.

The detector D1 may be used in common for reflectometry, ellipsometry, and transient optical embodiments of this invention. However, the resultant signal processing is different for each application. For transient optical measurements, the DC component of the signal is suppressed, such as by subtracting reference beam input D2, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of a rotating compensator (see discussion of FIG. 6, below), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The analysis can be performed by signal processor 101, or any suitable general-purpose-computer. The use of two beams is useful for improving resolution, and for resolving any ambiguities in the solution of the relevant equations.

A third beam splitter BS3 is used to direct a small fraction of the pump beam onto detector D4, which measures a signal proportional to the incident pump intensity. A fourth beam splitter BS4 is positioned so as to direct a small fraction of the pump beam onto detector D3, which measures a signal proportional to the reflected pump intensity.

Figure 6:
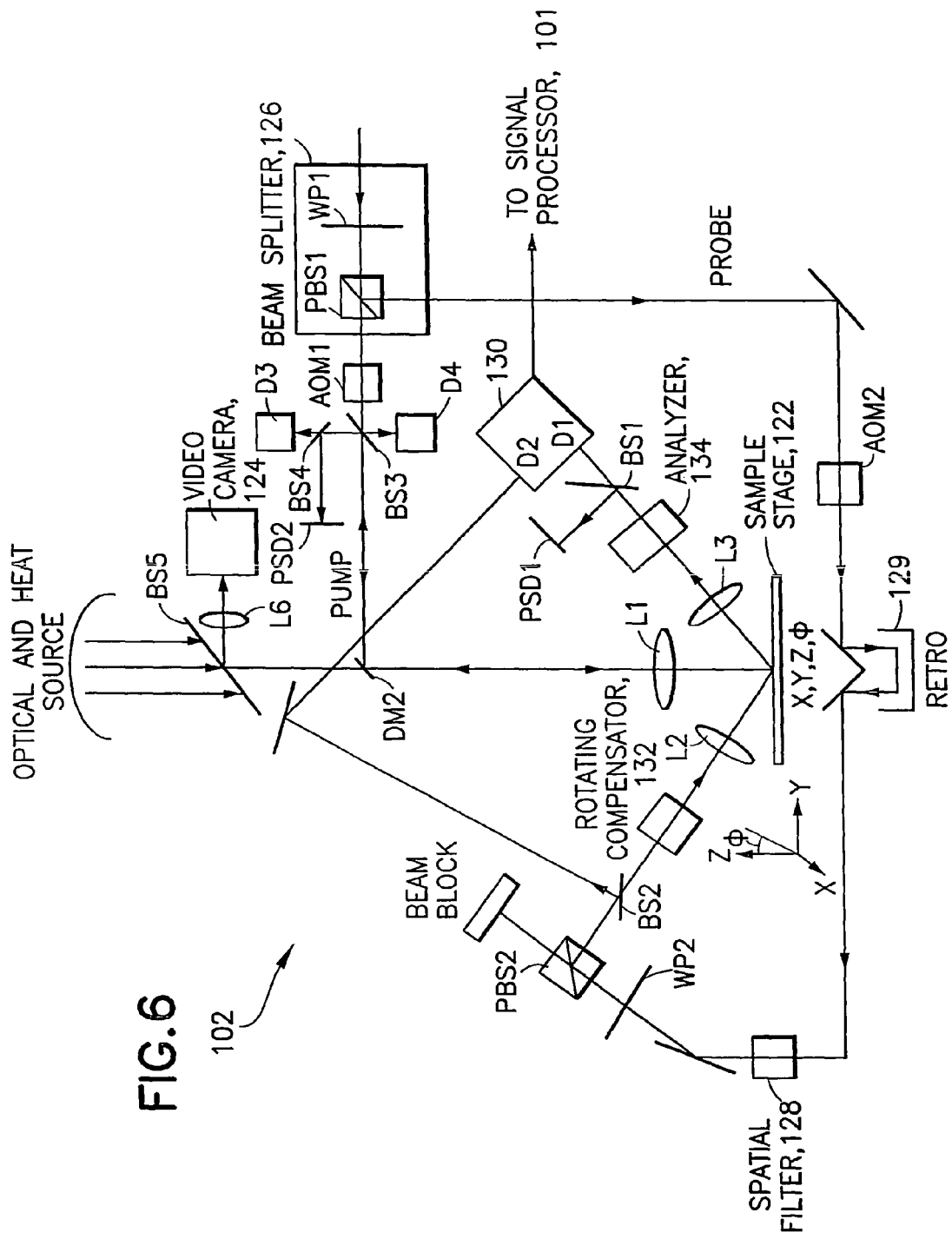
FIG. 6 is another embodiment of an ultra-fast optical system that is suitable for use in practicing this invention, specifically, a normal pump, oblique probe embodiment.

FIG. 6 illustrates a normal pump beam, oblique probe beam embodiment of apparatus 102. Components labeled as in FIG. 4 function in a similar manner, unless indicated differently below. In FIG. 6 there is provided the above-mentioned rotating compensator 132, embodied as a linear quarter wave plate on a motorized rotational mount, and which forms a portion of an ellipsometer mode of the system. The plate is rotated in the probe beam at a rate of, by example, a few tens of Hz to continuously vary the optical phase of the probe beam incident on the sample. The reflected light passes through an analyzer 134 and the intensity is measured and transferred to the processor 101 many times during each rotation. The signals are analyzed according to known types of ellipsometry methods to determine the characteristics of the sample (transparent or semitransparent films). This allows the (pulsed) probe beam to be used to carry out ellipsometry measurements.

The ellipsometry measurements are carried out using a pulsed laser, which is disadvantageous under normal conditions, since the bandwidth of the pulsed laser is much greater than that of a CW laser of a type normally employed for ellipsometry measurements. The ellipsometry measurement capability is useful in performing certain of the embodiments of the method described below, wherein it is an advantage to determine the index of refraction and thickness of one or more of the film layers disposed over the substrate.

Referring to FIG. 6, if transient optical measurements are being made, the rotating compensator 132 is usually oriented such that the probe beam is linearly polarized orthogonal to the pump beam. This is to reduce the amount of scattered pump light that can reach the detector of the reflected probe beam. As will be seen below, there may be samples for which there is an advantage to having the probe and pump beams with the same polarization. An analyzer 134 may be embodied as a fixed polarizer, and also forms a portion of the ellipsometer mode of the system. When the system is used for transient optical measurements the analyzer 134 is oriented to block the pump.

When used in the ellipsometer mode, the analyzer 134 is oriented so as to block light polarized at 45 degrees relative to the plane of the incident and reflected probe beam.

The embodiment of FIG. 6 further includes a dichroic mirror (DM2), which is highly reflective for light in a narrow band near the pump wavelength, and is substantially transparent for other wavelengths.

It should be noted in FIG. 6 that BS4 is moved to sample the pump beam in conjunction with BS3, and to direct a portion of the pump to D3 and to a second PSD (PSD2). PSD2 (pump PSD) is employed in combination with the processor 101, computer controlled stage 122 (tilt and z-axis), and PSD1 (probe PSD) to automatically focus the pump and probe beams onto the sample to achieve a desired focusing condition. Also, a lens L1 is employed as a pump, video, and optical heating focusing objective, while an optional lens L6 is used to focus the sampled light from BS5 onto the video camera 124.

Figure 7:
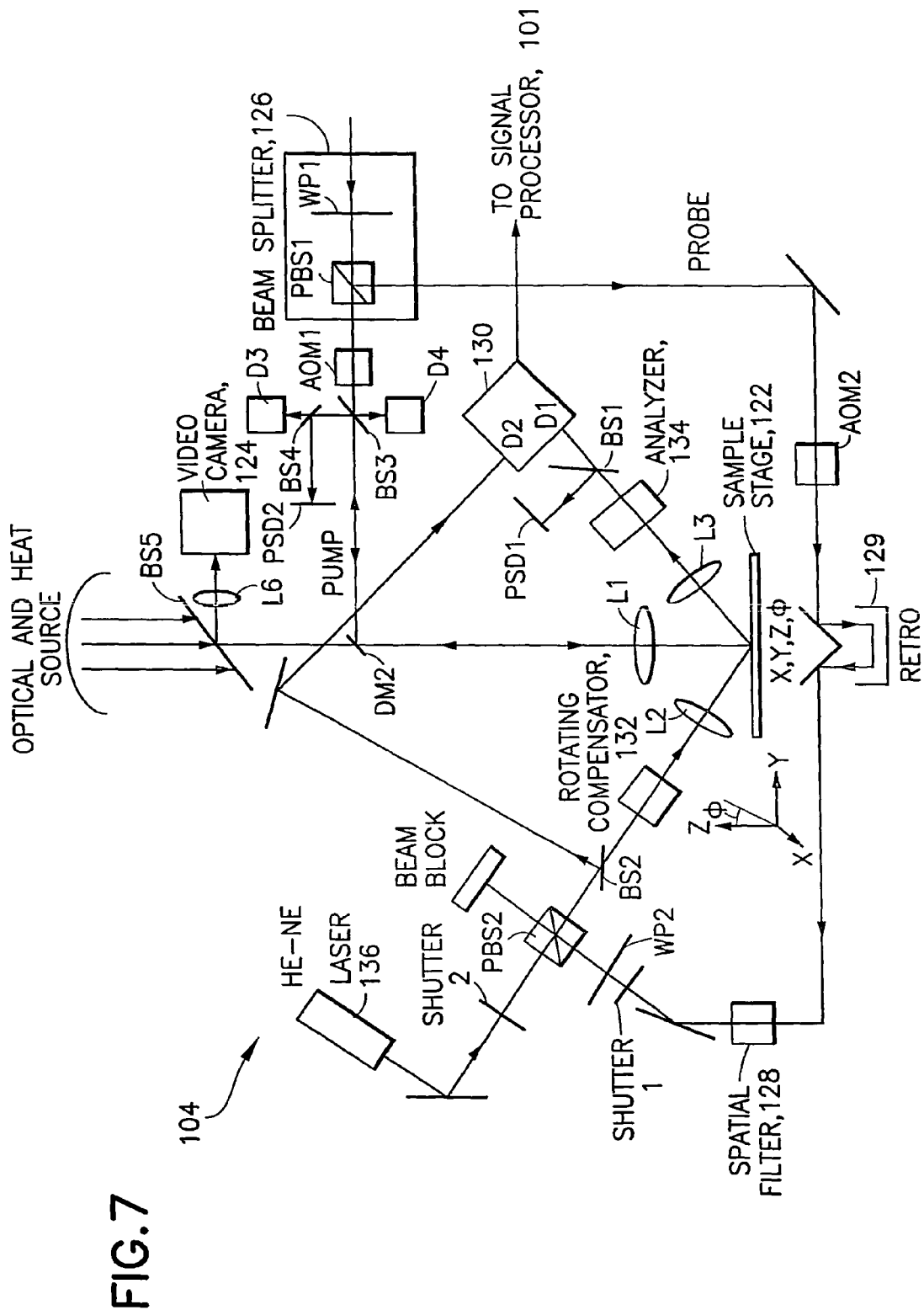
FIG. 7 is a block diagram of an other embodiment of an ultra-fast optical system that is suitable for use in practicing this invention, specifically, a single wavelength, normal pump, oblique probe, combined ellipsometer embodiment.

Reference is now made to FIG. 7 for illustrating an embodiment of apparatus 104, specifically a single wavelength, normal pump, oblique probe, combined ellipsometer embodiment. As before, only those elements not described previously will be described below.

Shutter 1 and shutter 2 are computer controlled shutters, and allow the system to use a He—Ne laser 136 in the ellipsometer mode, instead of the pulsed probe beam. For transient optical measurements shutter 1 is open and shutter 2 is closed. For ellipsometer measurements shutter 1 is closed and shutter 2 is opened. The He—Ne laser 136 is a low power CW laser, and has been found to yield superior ellipsometer performance for some films.

Figure 8:
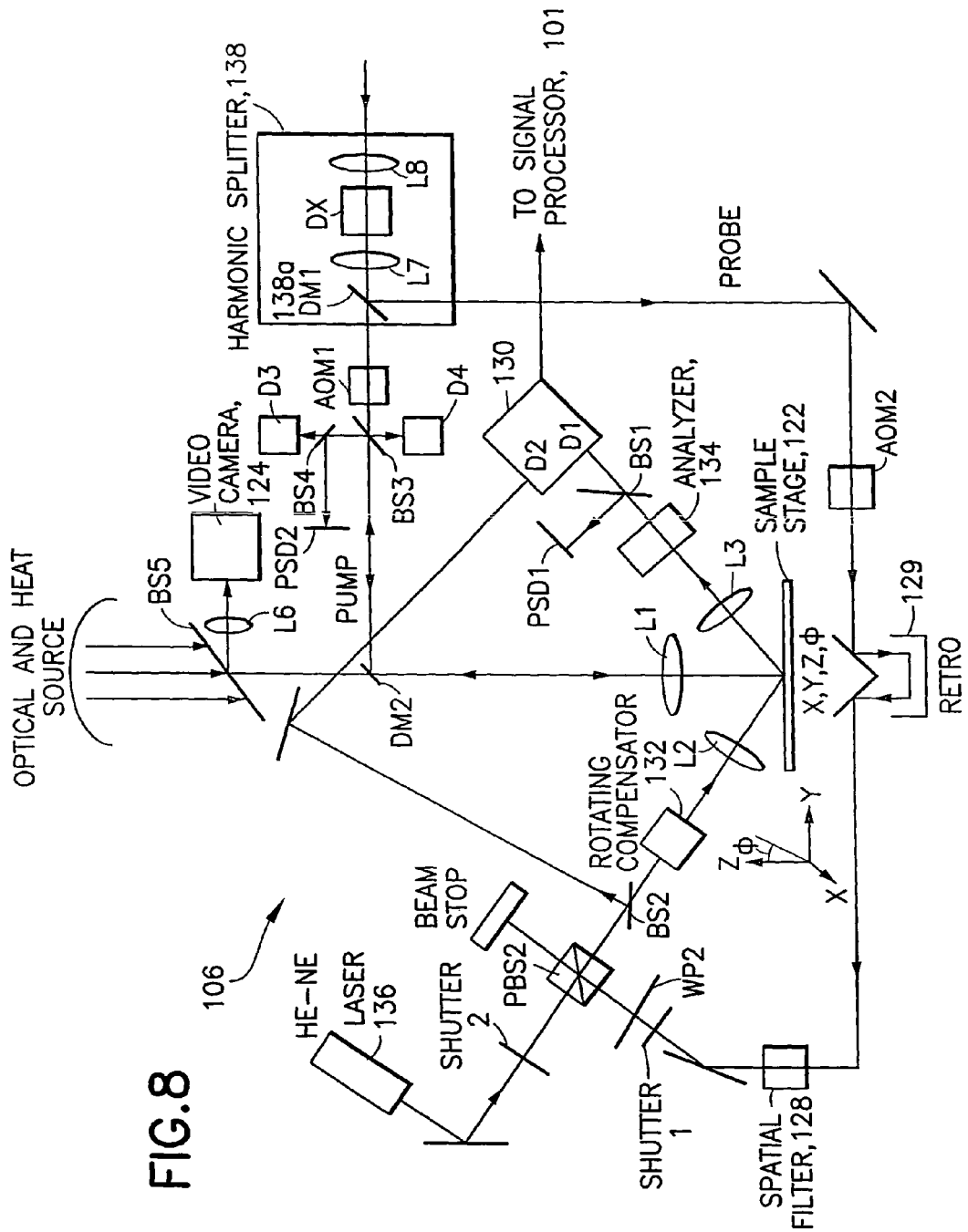
FIG. 8 is a block diagram of another embodiment of an ultra-fast optical system that is suitable for use in practicing this invention, specifically, a dual wavelength, normal pump, oblique probe, combined ellipsometer embodiment.

FIG. 8 is a dual wavelength embodiment 106 of the system illustrated in FIG. 7. In this embodiment the beam splitter 126 is replaced by a harmonic splitter 138, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM1 138a) to the AOM1, while the probe beam is reflected to the retroreflector. The reverse situation is also possible, i.e., the shorter wavelength may be transmitted, and the longer wavelength may be reflected, or vice versa. In the simplest case the pump beam is the second harmonic of the probe beam (i.e., the pump beam has one half the wavelength of the probe beam). It should be noted that in this embodiment the AOM2 can be eliminated and instead a color filter (not shown) can be used in front of the detector D1 in order to reduce the amount of pump light reaching the detector D1. The color filter is required to have high transmission for the probe beam and the He—Ne wavelengths, but very low transmission for the pump wavelength.

Figure 9:
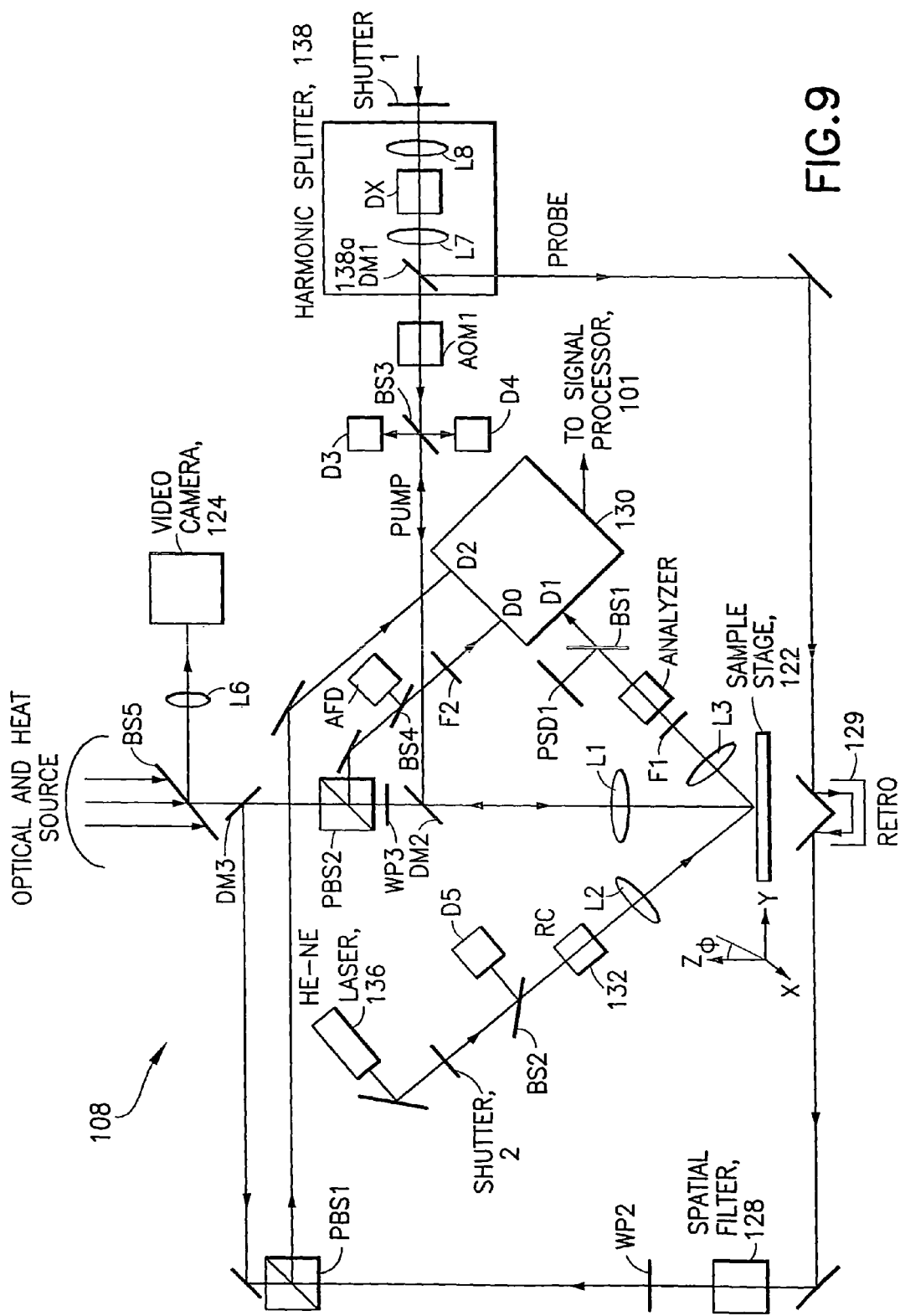
FIG. 9 is a block diagram of another embodiment of an ultra-fast optical system that is suitable for use in practicing this invention, specifically, a dual wavelength, normal incidence pump and probe, combined ellipsometer embodiment.

Finally, FIG. 9 illustrates a normal incidence, dual wavelength, combined ellipsometer embodiment 108. In FIG. 9 the probe beam impinges on PBS2 and is polarized along the direction which is passed by the PBS2. After the probe beam passes through WP3, a quarter wave plate, and reflects from the sample, it returns- to PBS2 polarized along the direction which is highly reflected, and is then directed to a detector D0 in detector block 130. D0 measures the reflected probe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths.

D1, a reflected He—Ne laser 136 detector, is used only for ellipsometric measurements.

Figure 10:
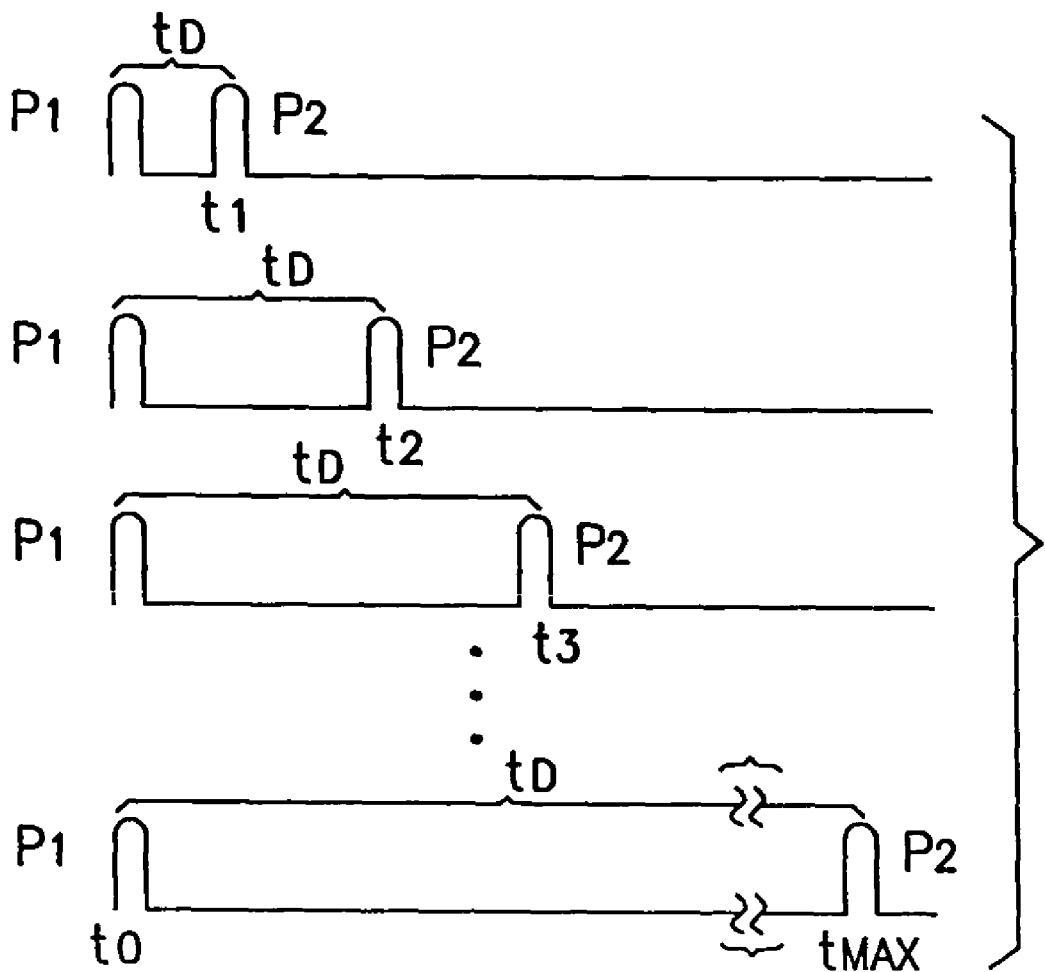
FIG. 10 illustrates a timed sequence of a plurality of consecutive pump pulses and corresponding probe pulses.

It should be noted when contrasting FIG. 9 to FIGS. 7 and 8, that the shutter 1 is relocated so as to intercept the incident laser beam prior to the harmonic splitter 138. Based on the foregoing descriptions, a selected one of these presently preferred embodiments of measurement apparatus provide for the characterization of samples in which a short optical pulse (the pump beam) is directed to an area of the surface of the sample, and then a second light pulse (the probe beam) is directed to the same or an adjacent area at a later time. The retroreflector 129 in all of the embodiments of FIGS. 3, 6, 7, 8 and 9 can be employed to provide a desired temporal separation of the pump and probe beams. FIG. 10 illustrates various time delays ($t_D$) between the application of a pump beam pulse (P1) and a subsequent application of a probe beam pulse (P2), for times ranging from $t_1$ to $t_{MAX}$.

If the sample includes a periodic array of structures disposed over a surface, the sample can act as a diffraction grating. Consequently, for some range of wavelength of the probe light there is a diffracted component, or components, to the reflected probe beam. Let $R_{diff}$ be the ratio of the power of one particular diffracted component of the probe light to the power of the incident probe beam, and let $\Delta R_{diff}(t)$ be the transient change in $R_{diff}$ induced by the application of the pump beam. For some samples it may be advantageous to measure $\Delta R_{diff}(t)$, rather than the change in the strength of the specularly reflected probe beam. This measurement can be made through the use of a second detector of reflected probe light that can be moved under computer control to a position so as to receive the diffracted component of the reflected probe beam. The position of this detector is determined by the following parameters: a) the spacing between the structures disposed on the surface of the sample; b) the wavelength of the incident probe light; and c) the angle of incidence of the probe light.

The five embodiments 100, 102, 104, 106 and 108, as described above, have in common the feature that a sequence of pump pulses are generated and directed at the surface of the sample. Each pump pulse illuminates the same area of the sample with an intensity that varies smoothly across the area. It is also within the scope of this invention to make, measurements of the transient optical response by means of the induced transient grating method. See: D. W. Phillion, D. J. Kuizenga, and A. E. Siegman, Appl. Phys. Lett. 27, 85 (1975).

To induce a transient grating each pump pulse is divided into two or more components by means of a beam splitter or beam splitters, these components then pass through separate optical paths, and are then all directed onto the same area of the surface of the sample. If the different components are directed onto the surface with different angles there are places within the area where the different components interfere constructively and places where the interference is destructive. Thus the total intensity of the pump light varies across the sample surface.

Figure 11:
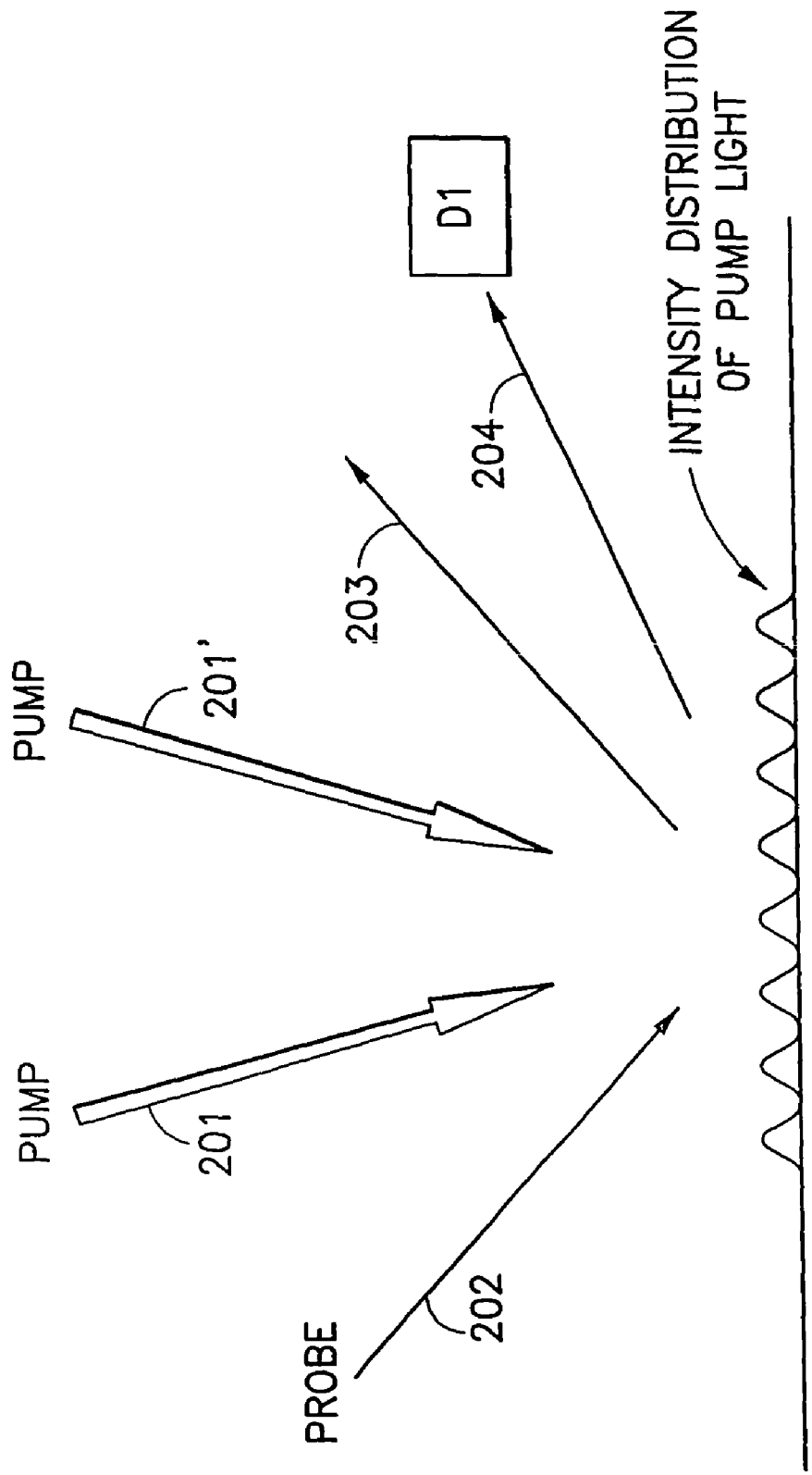
FIG. 11 illustrates the operation of a transient grating embodiment of this invention, wherein the pump pulse is divided and made to interfere constructively and destructively at the surface of the sample.

In the case that only two components 201 and 201' are present, as shown in FIG. 11, the intensity varies periodically across the sample surface. The periodicity of the intensity, i.e., the spacing between successive points of maximum intensity, is determined by the wavelength of the pump light and the angles at which the different components of the pump light are incident onto the surface. As a result of this periodic variation in the intensity, the amount of pump light absorbed in each structure is not the same, and also the amount of pump light absorbed in the films and the substrate varies periodically across the surface of the sample. The amplitude of the strain pulses that are generated thus varies periodically across the sample. Consequently, the transient changes in the optical properties of the sample, which result from the propagation of these strain pulses, also vary periodically. This variation of the transient changes in the optical properties of the sample is equivalent to the production of a transient diffraction grating coinciding with the sample surface. When probe light 202 is incident on the area excited by the pump, a part 204 of the probe light is diffracted, i.e., a part of the probe light is reflected in a direction, or directions, away from the direction 203 of specular reflection. Measurement of the intensity of this diffracted probe light by means of the detector D1 as a function of the time delay t between the application of the pump and probe beams provides an alternate method for the characterization of the transient optical response produced in the sample. Note that this mechanism for production of a diffracted probe beam is dependent on the generation of a periodic variation in the intensity of the pump beam, whereas the diffracted probe beam considered in the preceding section originates from the periodic arrangement of the structures on the sample surface. Furthermore, the use of the transient grating to determine the transient optical response of the sample can be employed in the various embodiments of measurement techniques described below for use with samples that include substructures.

Figure 12:
FIG. 12 illustrates a pulse train of pump beam pulses having an overlying low frequency intensity modulation impressed thereon.

Typical characteristics of the light pulses employed in the systems 100, 102, 104, 106, and 108, of FIGS. 3, 6, 7, 8 and 9, respectively, are as follows. The pump pulse has an energy of approximately 0.001 to 100 nJ per pulse, a duration of approximately 0.01 psecs to 100 psec per pulse, and a wavelength in the range 200 nm to 4000 nm. The pulse repetition rate (PRR) is in the range of 100 Hz to 5 Ghz and, as is shown in FIG. 12, the pump pulse train may be intensity modulated at a rate of 1 Hz to 100 MHz, depending on the PRR. The pump pulse is focused to form a spot on the sample surface of diameter in the range of approximately 10 micrometers to 20 micrometers, although smaller spot sizes, and hence better lateral resolution can also be employed.

Figure 13:
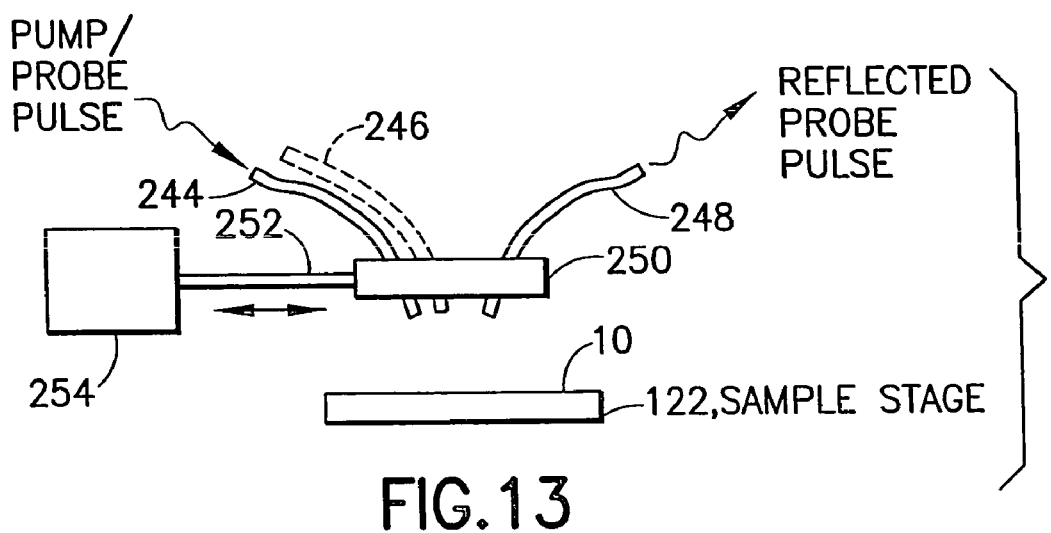
FIG. 13 illustrates a further embodiment wherein one or more optical fibers are positioned for delivering the pump beam and/or probe beam and for conveying away the reflected probe beam.

Referring to FIG. 13, it is also within the scope of the teaching of this invention to deliver the pump pulse, or the probe pulse, or both the pump and probe pulses, through an optical fiber 244. Alternatively, a second input fiber 246 can be provided, whereby the pump pulse is delivered through the fiber 244 and the probe pulse is delivered through the fiber 246. Another fiber 248 can also be employed for receiving the reflected probe pulse and delivering same to the photodetector (not shown). For this embodiment the ends of the optical fiber(s) are affixed to and supported by a holding stage 250. The holding stage 250 is preferably coupled through a member 252 to an actuator 254, such as a linear actuator or a two-degree of freedom positioning mechanism. In this manner the reliability and repeatability of the measurement cycle is improved, in that the size and position of the focused pump, probe, or pump and probe beams on the sample surface are independent of minor changes in the direction or profile of the laser output beams, or changes in the profile of the probe beam associated with the motion of any mechanical stage that may be used to effect the delay t. Preferably, the angular orientation between the end of the probe beam delivery fiber and the end of the reflected probe beam fiber is such as to optimize the gathering of reflected probe beam light from the sample surface. It is also within the scope of this invention to use one or more lenses following the fiber or fibers, in order to focus the output beams from the fibers onto the sample surface, or to collect the reflected probe light and to direct it into the fiber 248 of FIG. 13.

Figure 14:
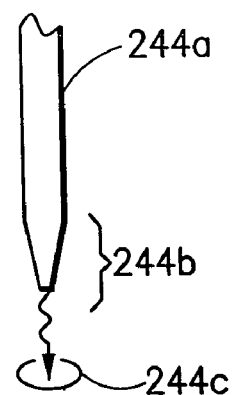
FIG. 14 is a side view a terminal end of a fiber optic that has been reduced in cross-sectional area for delivering an optical pulse to a small surface area of a sample.

FIG. 14 shows an embodiment wherein a terminal portion 244b of a pump and/or probe beam delivery fiber 244a is reduced in diameter, such as by stretching the fiber, so as to provide a focused spot 244c having a diameter that is less than the normal range of optical focusing. When coupled with the embodiment of FIG. 13 this enables the pump and or probe optical pulse to be repeatably delivered to a very small region of the sample surface, e.g., to a spot having a diameter<one micrometer, regardless of any changes that are occurring in the optical path length of the probe beam.

It is also within the scope of the invention to measure other transient optical responses instead of the change in the optical reflectivity. As previously mentioned, the apparatus 100, 102, 104, 106, and 108, as shown in FIGS. 3, 6, 7, 8 and 9, respectively, are capable of measuring the (1) transient change in the reflectivity $\Delta R(t)$ of the probe beam. With suitable modifications, the apparatus can be used to measure (2) the change $\Delta T$ in the intensity of the transmitted probe beam, (3) the change $\Delta P$ in the polarization of the reflected probe beam, (4) the change $\Delta \phi$ in the optical phase of the reflected probe beam, and/or (5) the change in the angle of reflection $\Delta \sigma$ of the probe beam. These quantities may all be considered as transient responses of the sample which are induced by the pump pulse. These measurements can be made together with one or several of the following: (a) measurements of any or all of the quantities (1)-(5) just listed as a function of the incident angle of the pump or probe light, (b) measurements of any of the quantities (1)-(5) as a function of more than one wavelength for the pump and/or probe light, (c) measurements of the optical reflectivity through measurements of the incident and reflected-average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

The measured results for $\Delta R(t)$, or other transient optical response, can be compared with simulations of the propagation of strain pulses in the sample. A complete simulation can be performed by the following steps:

a) The sample is described by a number of physical parameters, including but not limited to, the dimensions of each structure, the spacing between the structures, the thickness of any films making up the sample, the electrical resistivity of the sample material, etc. The electrical resistivity is a significant parameter because it affects the way strain pulses are generated in the sample as a result of the absorption of the pump pulse.

b) The absorption of the pump light pulse is then considered, and the change in temperature of each part of the sample is determined.

c) The thermal stress that results from this temperature change is calculated, and the amplitude of the generated strain pulses is determined.

d) The location of these strain pulses as a function of the time t is calculated and the time-dependent strain distribution in the sample is found.

e) From this strain distribution the change in optical reflectivity, or other transient optical response, is calculated and compared with the measured result.

f) The parameters of the sample are adjusted so as to obtain a best fit with the measured data.

Figure 15:
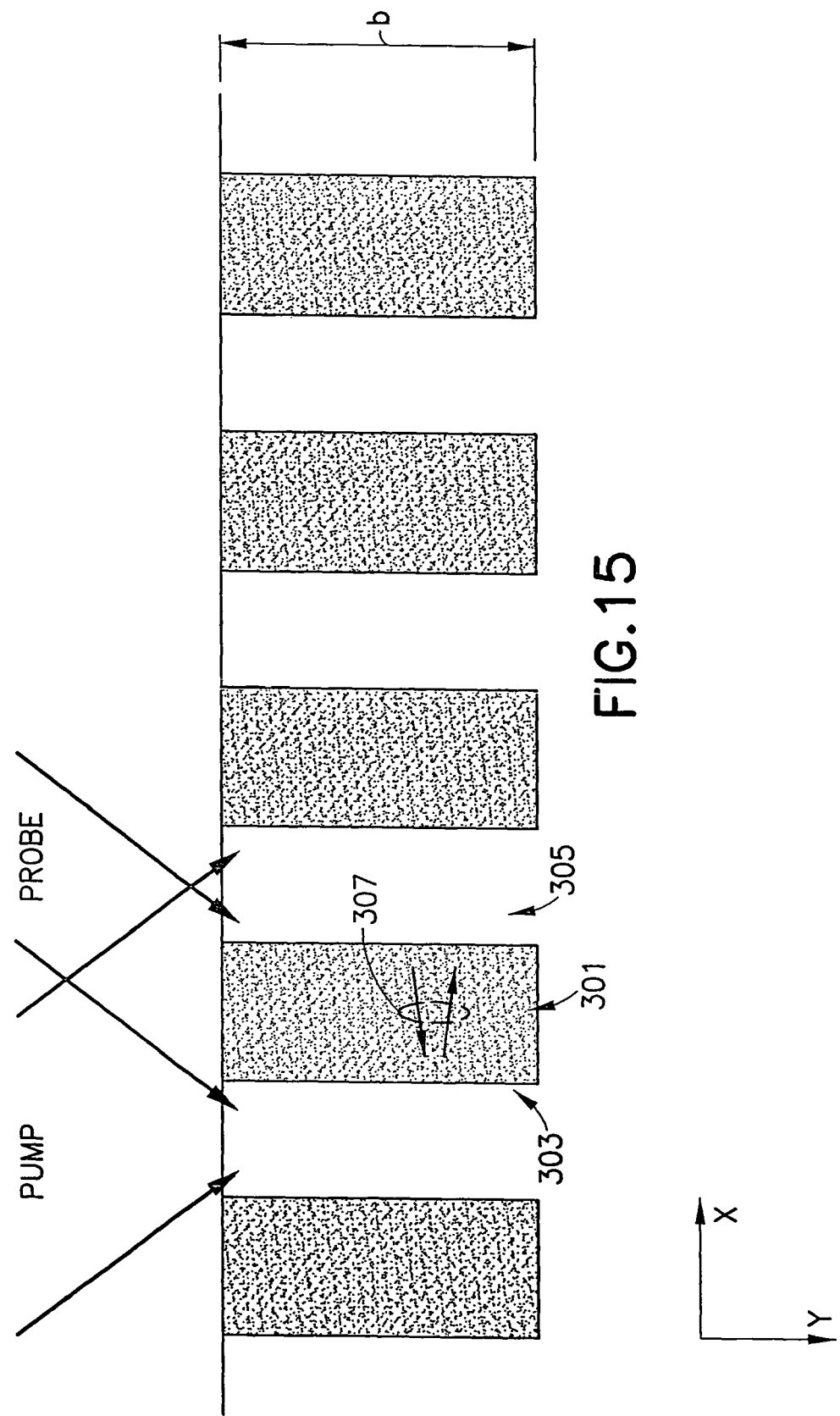
FIG. 15 is a sectional view of a two-dimensionally patterned sample composed of an array of wires each with rectangular cross-section embedded in a substrate.

For some samples, the available information may be insufficient to make an analysis of this type. In such samples a more limited approach may be used to obtain information about selected parameters of the sample. For example, FIG. 15 shows a sectional view of a two-dimensionally patterned sample composed of an array of structures, i.e. wires, each with rectangular cross-section embedded in a substrate 305. The pump and probe beams are directed at oblique incidence, i.e., neither perpendicular nor parallel to the surface of the sample. Absorption of the pump beam on the side wall 303 of each structure 301, generates a strain pulse 307 that propagates across the structure 301 and causes a change in the reflection of the probe beam. To model this particular contribution to $\Delta R(t)$, it may be sufficient to use a simplified approach. Since the side walls of the structure 301 are parallel, a measurement of the arrival time of the strain pulse is sufficient to determine the width of structure 301.

Figure 16:
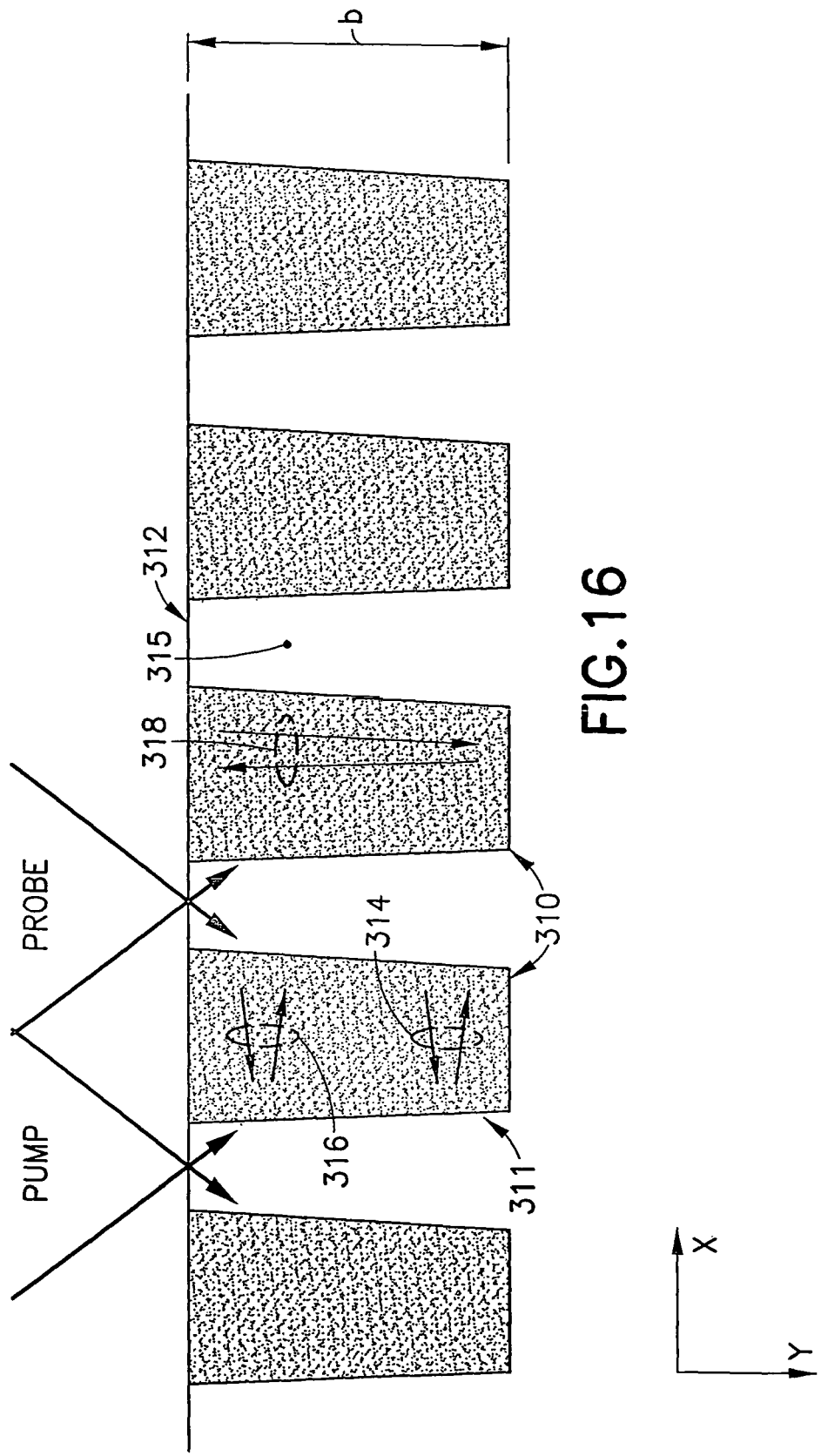
FIG. 16 is a-sectional view of a two-dimensionally patterned sample composed of an array of wires each with angled side walls embedded in a substrate where a pump beam and a probe beam are applied at oblique incidence.

In the event that the side walls are at a non-normal angle, as is shown for structure 310 in FIG. 16, the strain pulse is broadened because strain generated at different locations 314 and 316 on the side wall 311 of structure 310 travels a different distance to reach the far side of structure 310. Thus, an echo feature in $\Delta R(t)$ is broadened by an amount that increases with the angle of side wall 311.

A second acoustic pulse 318 is generated at the top surface of structure 310 and travels in the direction perpendicular to the plane 312 of substrate 315. This gives rise to a separate series of echoes whose spacing in time can be used to measure the height b of structure 310.

It is also within the scope of this invention to detect echoes arising from the part of the strain pulse that is reflected at boundaries within a structure. For example, in FIGS. 17 and 18 each structure includes a wire 320 of one material with a liner 325 of another material, e.g., an oxide, on each side. Pump light that is absorbed on the sides of the wire 320 generates a strain pulse at the surface 330 of liner 325. This strain pulse is partially reflected at the interface between the liner 325 and the core material of the wire 320. The part of the strain returning directly to the outer surface of the liner 325 gives rise to an echo feature. From the time at which this echo occurs, the thickness of liner 325 can be found.

It is also within the scope of the invention to make measurements on samples composed of structures with dimensions so small that the spatial extent of the generated strain pulse is comparable to the thickness, or width, of the structure. For such samples it is not as useful to consider that the generated strain pulse bounces back and forth within the sample. Instead, one should consider that the pump pulse excites each structure into one or more of its normal modes of vibration. Under these conditions, the change in optical reflectivity $\Delta R(t)$ varies with time t as a sum of a number of oscillatory components with different frequencies and damping rates. These frequencies and damping rates can be determined from the measured $\Delta R(t)$ by the following methods:

(a) The Fourier transform of $\Delta R(t)$ is taken. Peaks in the Fourier spectrum are identified with the normal mode frequencies. The widths of the peaks can be used to give the damping rates of the individual normal modes.

(b) The measured $\Delta R(t)$ can be fit to a sum of damped oscillations with different frequencies. This fitting process can be accomplished through the use of a standard non-linear least squares fitting algorithm.

Other analysis methods will be apparent to those skilled in the art, when guided by the foregoing teachings in accordance with the present invention.

The results for the frequencies and damping rates can then be compared with frequencies and damping rates obtained from a computer simulation of the vibrations of the sample. In more detail:

a) The sample is described by a number of physical parameters, including but not necessarily limited to, the dimensions of each structure, the spacing between the structures, the thickness of any films making up the sample, etc.

b) The frequencies and the damping rates are calculated using, for example, a finite-element simulation of the vibrations of the structure.

c) Steps (a) and (b) are repeated with each physical parameter varied over a suitable range.

d) The measured frequencies and damping rates are compared with the calculated frequencies and damping rates obtained for each set of parameters, and the set of parameters that gives frequencies and damping rates closest to those measured is determined.

Variations of this method may include, but are not limited to:

i) Use of methods other than finite-element simulation to calculate the frequencies and damping rates. For example, a molecular dynamics approach may be more suitable for some samples.

ii) The method as described above amounts to the establishment of a catalog of frequencies and damping rates for a range of physical parameters. An alternate method starts from some initial set of physical parameters, compares the frequencies and the damping rates to the measured frequencies and damping rates, and then repeatedly adjusts the physical parameters so as to improve the agreement between simulation and experiment, until a best fit is obtained.

iii) Use of the amplitude of the contributions from the different modes to give information about the physical parameters of the sample. For example, the modes that have a large strain amplitude in the regions where the pump pulse is strongly absorbed will have a large amplitude.

The list of physical parameters can include the adhesion of one part of each structure to another, the adhesion between the structure and the film or films in which it is embedded or disposed upon, and the sound velocity and density of the different components of the sample.

Figure 17:
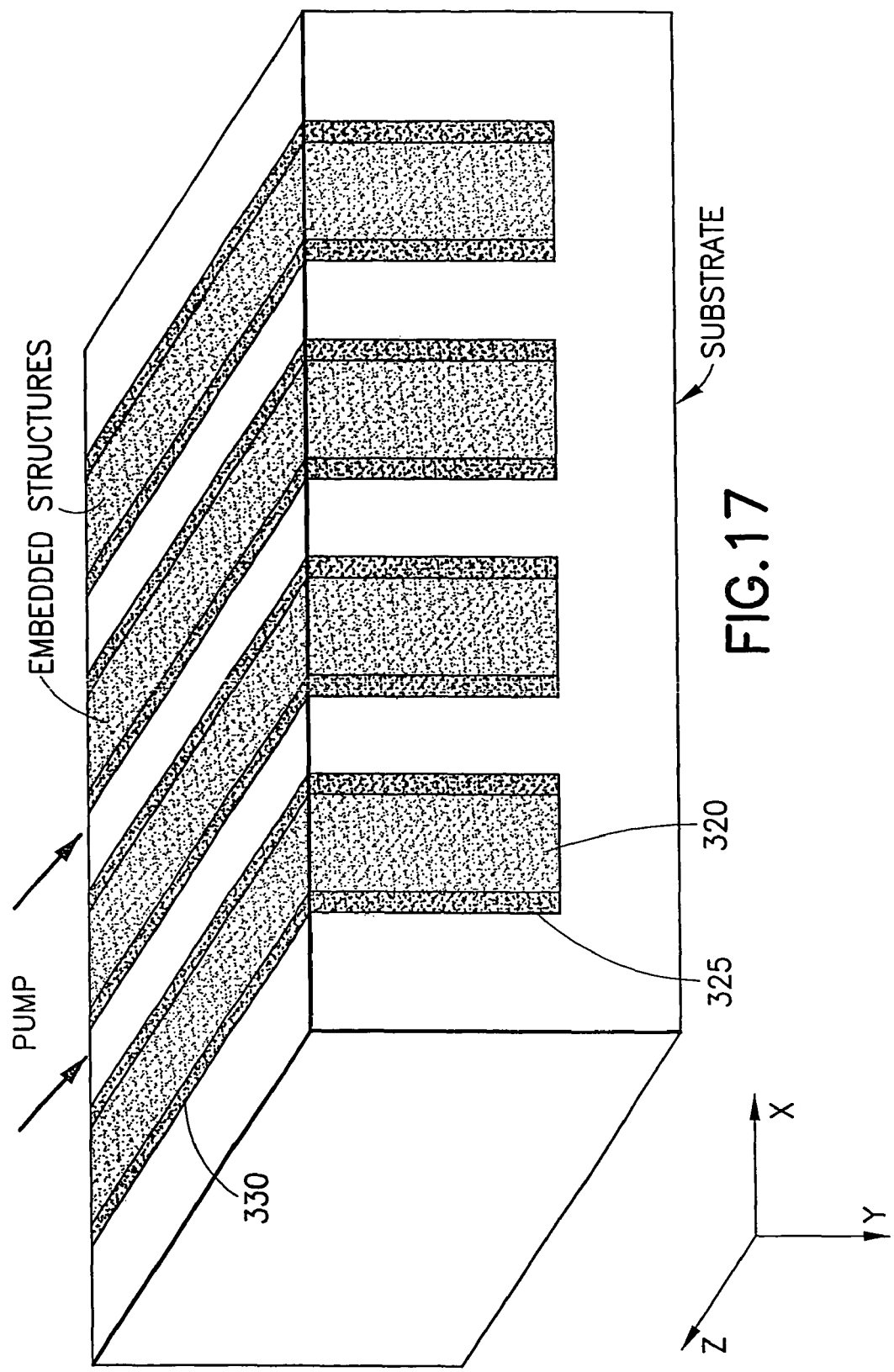
FIG. 17 is a perspective view of a two-dimensionally patterned sample composed of an array of wires embedded in a substrate, where each wire has a coating on its sides, and where a pump beam is applied at oblique incidence.
Figure 18:
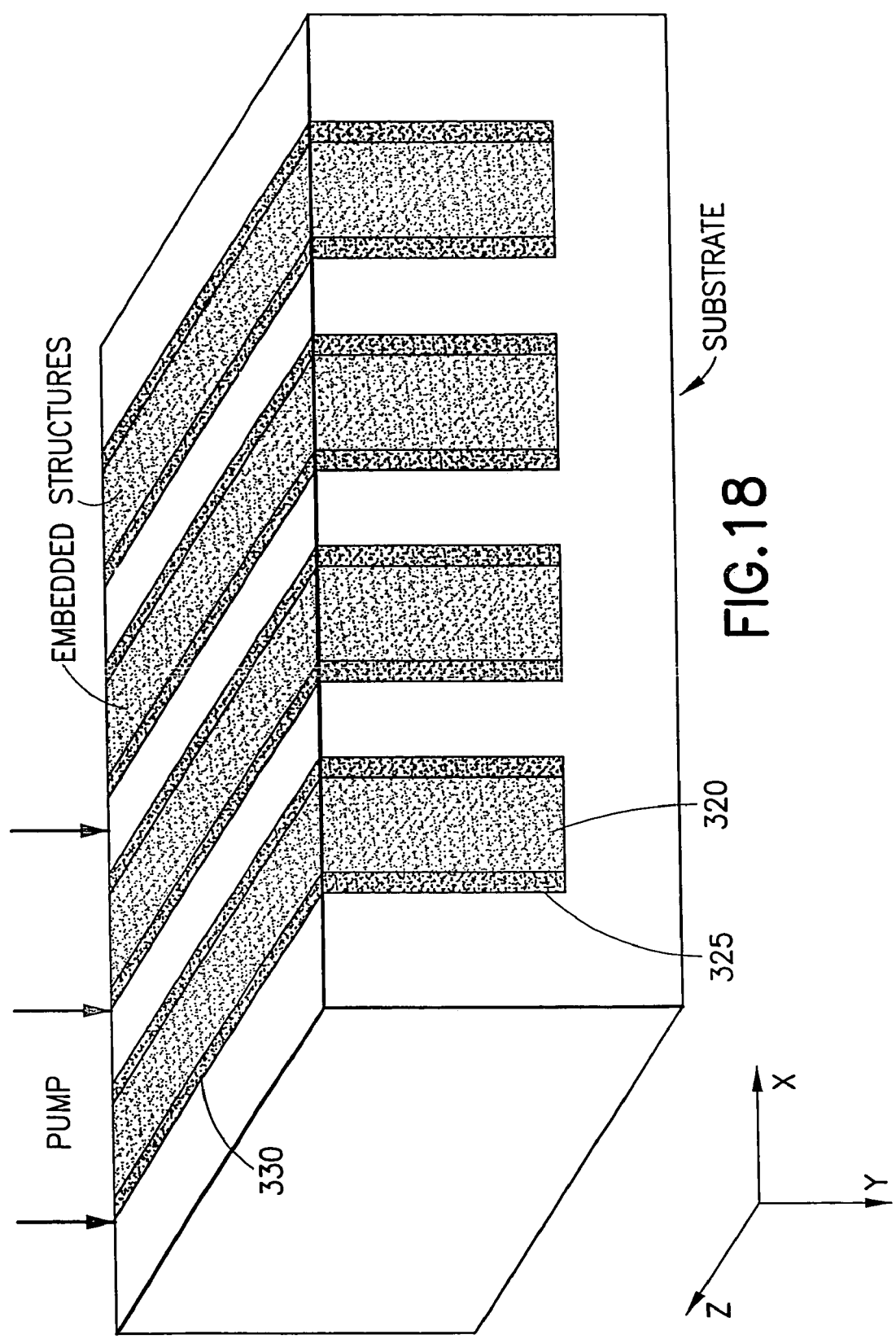
FIG. 18 is a perspective view of a two-dimensionally patterned sample composed of an array of wires embedded in a substrate, where each wire has a coating on its sides, and where a pump beam is applied at normal incidence.

For some samples, it is advantageous to make measurements with particular choices of the angle of incidence of the pump and/or the probe beam. There may be advantages to particular choices of the polarization of these beams. In addition, it may be advantageous to measure the sample for more than one selection of the angles of incidence and polarization. The reasons for this include:

a) Achievement of a better signal to noise ratio. This can reduce the time for the measurement to be made.

b) Enhancement of some features of particular interest relative to other features that are readily apparent in the measured $\Delta R(t)$, but which are less important. For example, in FIG. 17 is shown a two-dimensionally patterned sample composed of an array of wires embedded in a substrate. Each wire 320 has a liner 325 in the form of a thin slab of a different material on its sides. If it is desired to measure the thickness of the liner 325 it may be favorable to direct the pump beam in a direction in the x-y plane at oblique incidence to the sample surface so that a large part of the beam is absorbed in liner 325. This enhances the amplitude of echoes arising from a strain pulse bouncing back and forth in liner 325. The amount of energy absorbed in the liner 325 may also be increased through appropriate choice of the polarization of the pump beam. The magnitude of the echo appearing in $\Delta R(t)$ due to the strain pulse in the coating may be further enhanced through a suitable choice of the direction of the probe beam and by choice of the polarization of the probe beam.

c) Simplification of the identification of the vibrational modes. An essential part of the method described above is the identification of individual measured mode frequencies with frequencies of modes obtained by the simulation. To aid in this identification process it is helpful for some samples to take advantage of the symmetry of the normal modes. For example, in FIG. 18 is shown the same sample as is shown in FIG. 17, but now the pump beam is directed at normal incidence. For this sample the y-z plane is a plane of mirror symmetry. It is clear that when excited in this way only modes for which the strain is an even function of x are excited (even modes). For these modes the displacement is an odd function of x. Thus, the measured $\Delta R(t)$ includes a sum of oscillations whose frequencies should be compared only with the frequencies of the modes from the simulation that have the same symmetry, i.e., even modes. Thus, one possible procedure is the following:

i) Measure the sample with a pump beam at normal incidence as shown in FIG. 18, and determine the frequencies and damping rates of the normal modes (even symmetry modes).

ii) Identify these modes with modes of even symmetry obtained from the simulation.

iii) Change the orientation of the pump beam to oblique incidence, and determine a new set of frequencies and damping rates. This set contains frequencies not present in the set obtained in i). These frequencies are likely to correspond to modes with odd symmetry (strain an odd function of x).

For some samples the same advantages just described may also ensue from measurement of changes in the diffracted probe beam. Corresponding advantages may also result from the use of the transient grating method.

For laterally-patterned samples in which the structures form an array, it is also within the scope of this invention to use the angle of diffraction of the pump and/or the probe beam to deduce the repeat distance of the array of structures. It is also within the scope of this invention to supply a separate light beam, e.g., a He—Ne laser, to the sample, to measure the angle of diffraction of this beam, and to calculate the repeat distance of the array from this diffraction angle. This repeat distance can be used as an input to the analysis.

It is also within the scope of this invention to use a combination of simulations of propagating strain pulses and normal mode analysis. For example, the part of $\Delta R(t)$ corresponding to early times may show sharp features best analyzed in terms of echoes due to strain pulses, while the part of $\Delta R(t)$ at longer times may be better described in terms of normal modes.

It is within the scope of this invention for the pump and probe beams to be focused so that they illuminate a large number of the similar structures that make up the sample, or just a few of these structures. In the event that only a few structures are illuminated it may not be possible to detect a diffracted probe beam.

In some samples there may be cracks or voids or other mechanical defects within one element of the structure, as distinct from poor adhesion of a structure element to the film, or films, in which it is embedded. Such defects may make a large change in the frequency and damping rate of certain of the normal modes. From the determination of which modes are affected and the extent of the changes in frequency and damping, it is possible to determine the location and size of the defect. For example, the effect of a defect on a mode is large if it is at a position in the sample where the oscillating strain due to the normal mode is large. It is also within the scope of this invention to identify such defects by comparison with measurements on samples known to contain certain defects.

In addition to the contribution to the change in reflectivity from the propagating strain pulses, there is a contribution to the measured $\Delta R(t)$ from temperature changes induced in the sample by the application of the pump light pulse. A change in temperature results in a change in the optical constants of a material, this effect being referred to as thermo-reflectance. The thermo-reflectance contribution to $\Delta R(t)$ is a smoothly varying function of time, and is thus readily distinguishable from the contribution due to the strain pulses which includes a series of echoes or oscillations. For some samples, from an analysis of the thermo-reflectance contribution to $\Delta R(t)$ it is possible to determine the rate of change in temperature of different parts of the sample. From this rate of change, it may be possible to estimate the thermal conductivity of one or more of the elements making up the sample, or to determine the Kapitza conductance at one or more of the interfaces between the different components of the sample, for example, between each structure and the film or films in which it is embedded or disposed upon. The Kapitza conductance is enhanced at interfaces where the materials are in intimate contact, and thus can be used as a measure of the adhesion at an interface.

If the structures making up a laterally patterned sample have a variation in their dimensions, the frequency of the normal modes varies from structure to structure. When some number of these structures are set into vibration by the pump light pulse, the vibrations in each structure is initially in phase. As time progresses, however, the vibrations become out of phase, resulting in an increased damping of the oscillation appearing in the measured $\Delta R(t)$. It is within the scope of this invention to use a measurement of this increased damping rate to characterize the variation in the dimensions of the structures within the measurement region.

Figure 19:
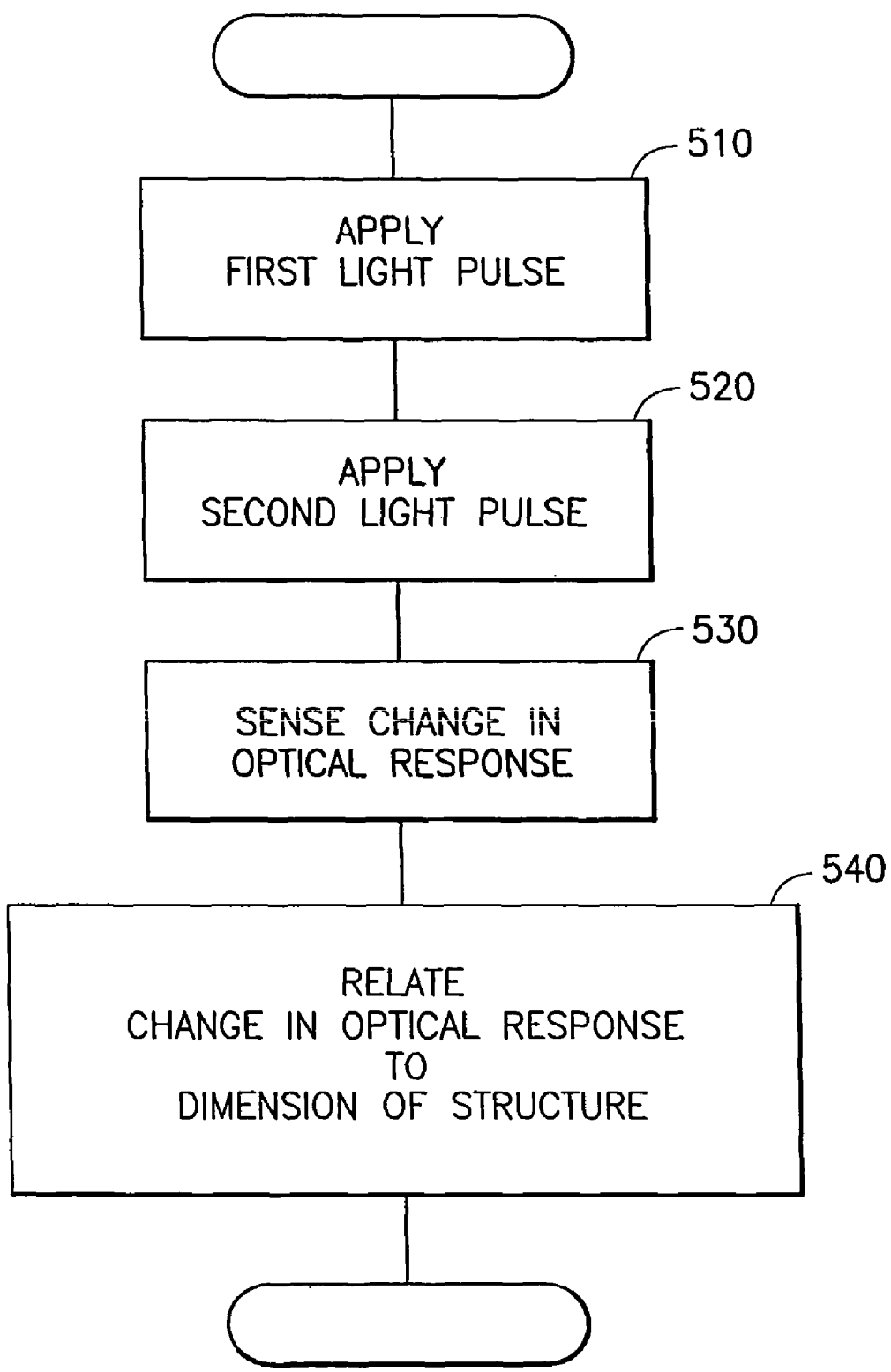
FIG. 19 is a flowchart of a method for characterizing a sample by relating a change in optical response to a dimension of the structure in accordance with the present invention.

FIG. 19 is a flowchart of one method for characterizing a sample in accordance with the present invention. The sample includes a structure disposed on or within the sample.

In step 510, a first pulse of light is applied to a surface of the sample for creating a propagating strain pulse in the sample.

In step 520, a second pulse of light is applied to the surface so that the second pulse of light interacts with the propagating strain pulse in the sample.

In step 530, a change in optical response of the sample is sensed from a reflection of the second pulse.

In step 540, a time of occurrence of the change in optical response is related to at least one dimension of the structure.

Figure 5:
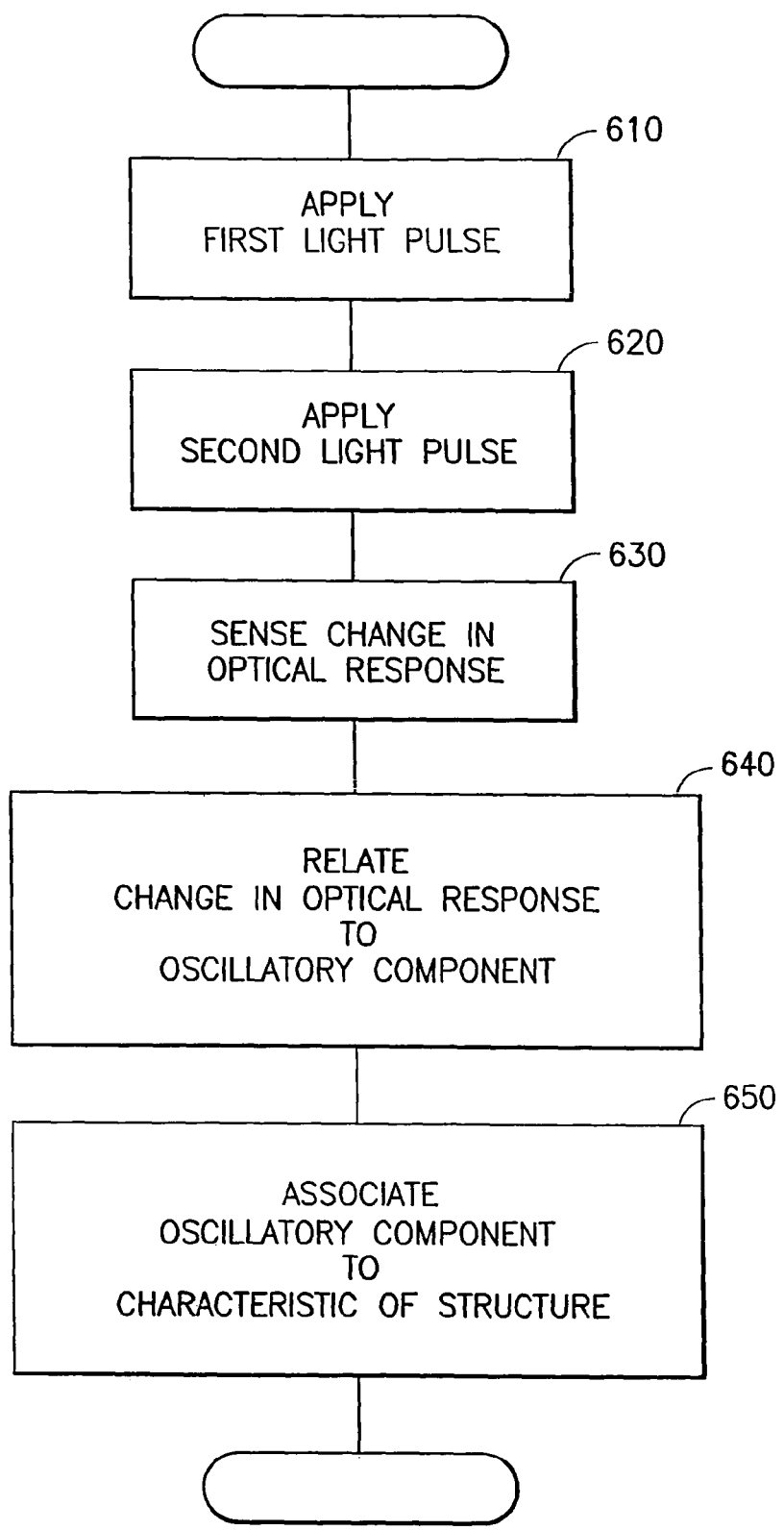
FIG. 5 is a flowchart of a method for characterizing a sample by evaluating an oscillatory component of the sample in accordance with the present invention.

FIG. 5 is a flowchart of a second method for characterizing a sample in accordance with the present invention. The sample includes a structure disposed on or within the sample.

In step 610, a first pulse of light is applied to a surface of the sample to excite the structure into a vibration in at least one of its normal modes.

In step 620, a second pulse of light is applied to the surface.

In step 630, a change in optical response of the sample is sensed from a reflection of the second pulse.

In step 640, the change in optical response is related to an oscillatory component of the vibration.

In step 650, the oscillatory component is associated to at least one of a spatial or electrical characteristic of the structure.

The present invention can be used to characterize structures made of any metal or metal alloy including copper, cobalt, titanium, aluminum, gold, nickel, silver, tungsten, etc. The invention can also be used to characterize polysilicon gate structures, and polysilicon gate structures onto which a metal contact layer has been deposited. The sample can be any semiconductor material, for example, a Group IVA semiconductor, a Group IIB-VIA semiconductor (e.g., HgCdTe, InSb), a Group IIIA-VA semiconductor (e.g., GaAs, GaAlAs), or combinations thereof. In addition, the sample may comprise a desired non-semiconductor layer, such as a substrate or an overlayer, comprised of a glass, sapphire or diamond.

While the invention has been particularly shown and described with respect to preferred embodiments thereof, it will be understood by those skilled in the art that changes in form and details may be made therein without departing from the invention. Accordingly, the present invention is intended to embrace all such alternatives, modifications and variances that fall within the scope of the appended claims.

What is claimed is:

1. A method comprising:
   applying a first pulse of light to a surface of the sample for creating a propagating strain pulse in a sample, where the sample comprises a plurality of structures disposed on or within the sample;
   applying a second pulse of light to the surface so that the second pulse of light interacts with the propagating strain pulse in the sample;
   sensing from a reflection of the second pulse a change in optical response of the sample; and
   relating a time of occurrence of the change in optical response to at least one dimension of the structure,
   where relating comprises:
   applying a beam of light to the surface so that the beam of light generates a diffracted beam of light;
   determining at least one characteristic of the diffracted beam of light; and
   calculating a characteristic of the plurality of structures based at least in part on the at least one characteristic of the diffracted beam of light.

2. A method as in claim 1, where the at least one characteristic comprises at least one of: an intensity of the diffracted beam of light and a phase of the diffracted beam of light.

3. A method as in claim 1, where at least one of the first pulse and second pulse is applied at oblique incidence.

4. A method as in claim 1, where at least one of the first pulse and second pulse is applied with a predetermined polarization.

5. A method as in claim 1, where the structure comprises a metal or metal alloy.

6. A method as in claim 1, where the sample comprises a semiconductor material.

7. A method as in claim 1, where the sample comprises at least one layer of a non-semiconductor material.

8. A method as in claim 1, further comprising moving a detector to receive the diffracted component of the beam of light.

9. A method as in claim 1, further comprising applying a second light beam to the sample generating a diffracted second beam of light and determining at least one characteristic of the diffracted second beam of light, where calculating a characteristic of the plurality of structures is further based at least in part upon the at least one characteristic of the diffracted second beam of light.

10. A method as in claim 1, where the at least one dimension is a width of the structure.

11. A method as in claim 1, further comprising performing at least one ellipsometry measurement of the sample.

12. The method as in claim 1, where the beam of light is generated by a laser.

13. The method as in claim 12, where the laser is an He—Ne laser.

14. The method as in claim 1, where the characteristic of the plurality of structures is a repeat distance.

15. A system comprising:
    an optical source unit configured to apply a first pulse of light to a surface of a sample for creating a propagating strain pulse in the sample, and to apply a second pulse of light to the surface so that the second pulse of light interacts with the propagating strain pulse in the sample, where the sample comprises a plurality of structures disposed on or within the sample;
    where the optical source unit is further configured to apply a beam of light to the surface to generate a diffracted beam of light;
    a sensor configured to sense a reflection of the second pulse a change in optical response of the sample; and
    a processor configured to relate a time of occurrence of the change in optical response to at least one dimension of the structure,
    where the processor is further configured to determine at least one characteristic of the diffracted beam of light and calculate a characteristic of the plurality of structures based at least in part on the determined at least one characteristic of the diffracted beam of light.

16. A system as in claim 15, where the processor is further configured to compare the time of occurrence to a result of a computer simulation of a propagation of the strain pulse in the sample.

17. A system as in claim 15, where at least one of the first pulse and second pulse is applied at oblique incidence.

18. A system as in claim 15, further comprising at least one polarizer, where at least one of the first pulse and second pulse is polarized with the at least one polarizer to have a predetermined polarization.

19. A system as in claim 15, further comprising a detector configured to be moved to receive the diffracted component of the beam of light.

20. A system as in claim 15, further comprising an ellipsometer.

21. A non-destructive system comprising:
    a first pulse applying means for applying a first pulse of light to a surface of a sample for creating a propagating strain pulse in the sample, where the sample comprises a plurality of structures disposed on or within the sample,
    a second pulse applying means for applying a second pulse of light to the surface so that the second pulse of light interacts with the propagating strain pulse in the sample;
    a beam applying means for applying a beam of light to the surface to generate a diffracted beam of light;
    a sensing means for sensing from a reflection of the second pulse a change in optical response of the sample; and
    a relating means for relating a time of occurrence of the change in optical response to at least one dimension of the structure, where the relating means is further for determining at least one characteristic of the diffracted beam of light; and calculating a characteristic of the plurality of structures based on the determined at least one characteristic of the diffracted beam of light.

22. A system as in claim 21, where the first pulse applying means, second pulse applying means and beam applying means is an optical source unit; the sensing means is a sensor; and the relating means is a processing unit.

23. A system as in claim 21, further comprising a means for making an ellipsometry measurement.

\* \* \* \* \*